United States Patent [19]
Lindberg et al.

[11] Patent Number: 4,795,803
[45] Date of Patent: Jan. 3, 1989

[54] ADHESIN ANTIGENS, ANTIBODIES AND DNA FRAGMENT ENCODING THE ANTIGEN, METHODS AND MEANS FOR DIAGNOSIS AND IMMUNIZATION ETC.

[75] Inventors: Frederick C. Lindberg, Sandviken; Björn O. Lund, Umea; Britt M. Båga, Umeå; Mari E. Norgren, Umeå; Mikael Goransson, Umeå; Bernt E. Uhlin, Umeå; Jan S. Normark, Holmsund; David L. Lark, Umeå, all of Sweden

[73] Assignee: Syn-Tek AB, Umeå, Sweden

[21] Appl. No.: 817,849

[22] PCT Filed: May 2, 1985

[86] PCT No.: PCT/DK85/00045
§ 371 Date: Feb. 19, 1986
§ 102(e) Date: Feb. 19, 1986

[87] PCT Pub. No.: WO85/05037
PCT Pub. Date: Nov. 21, 1985

[30] Foreign Application Priority Data
May 2, 1984 [DK] Denmark ............................ 2190/84

[51] Int. Cl.⁴ ...................... A61K 39/02; C07K 15/00; C07K 15/04
[52] U.S. Cl. ...................... 530/324; 424/92; 435/820; 436/543; 530/325; 530/326; 530/327; 530/328; 530/329; 530/330; 530/350; 530/403; 530/806; 530/825; 935/65

[58] Field of Search ............... 530/334, 335, 350, 403, 530/806, 825, 324–330; 435/7, 820; 436/543; 424/92; 935/65

[56] References Cited
U.S. PATENT DOCUMENTS

| 4,157,390 | 6/1979 | Parry et al. | 424/92 |
| 4,443,431 | 5/1984 | Buchanan et al. | 530/350 |
| 4,454,117 | 6/1984 | Brinton | 424/92 |
| 4,521,334 | 6/1985 | Beachey | 530/806 |
| 4,652,448 | 3/1987 | Sadowski | 436/548 |
| 4,657,849 | 4/1987 | Källenius et al. | 530/403 |

OTHER PUBLICATIONS
G. Dougan et al., Journ. Bact. 153, 364–370 (1983).
F. R. Mooi et al., Journ. Bact. 150, 512–521 (1982).

Primary Examiner—Robert J. Warden
Assistant Examiner—David A. Saunders
Attorney, Agent, or Firm—John P. White

[57] ABSTRACT

An antigen which, as its major immunizing component, comprises a determinant of an adhesin polypeptide or an immunogenically active subsequence thereof or a precursor therefor which is convertible to an immunogenically active form, antibodies against which determinant react with the adhesion polypeptide produced by pathogenic adhesin-forming bacteria which adhere to mammalian tissue, antibodies against such antigen, and DNA expressing, as a principal gene product thereof, such antigen.

10 Claims, 3 Drawing Sheets

ADHESIN ANTIGENS, ANTIBODIES AND DNA FRAGMENT ENCODING THE ANTIGEN, METHODS AND MEANS FOR DIAGNOSIS AND IMMUNIZATION ETC.

The present invention relates, inter alia, to an antigen useful, e.g., for the immunization of a mammal, an antibody raised against it, and a vaccine produced from it.

Antigens composed of several proteins which together form a distinct phenotype in a pathogenic bacterial strain or species, and which must therefore be assumed to contain a large number of immunogenic determinants, are well known. However, such antigens—and vaccines produced from them—have a number of disadvantages: in particular, they have a tendency to be too selective in that, on immunization, antibodies are formed against each of these immunogenic determinants which together identify the one particular bacterial strain from which the antigen has been derived, but not other bacterial strains of the same species so that immunization is only effected against this particular strain, but not other, closely related strains of the same species.

The present invention is an attempt to overcome these disadvantages by providing an antigen which substantially only comprises the immunogenic determinant(s) which lead to the desired immunity and which is furthermore not limited to one particular strain of the pathogenic bacteria in question.

It has become increasingly clear that the capacity of many pathogenic bacteria to adhere to the surface of cells is of primary importance for the initiation of many infectious diseases (Beachey, *J. Infect. Dis.* 143, 1981, pp. 325–345). This adhesion capacity is caused by the presence of receptors on mammalian tissue cells, such as epithelial cells, or on mammalian erythrocytes, which receptors, due to their configuration, form bonds with adhesin polypeptides. (In the present context, the term "adhesin polypeptide" is intended to indicate both a polypeptide specifically required for the adhesion phenotype and, more generally, a polypeptide in whose absence adhesion does not take place (for whatever reason). Each receptor is assumed to bond with a different adhesin structure. The receptor may be a peptide receptor, such as an amino acid present on a sugar, or—more usually—a carbohydrate such as neuramic acid-$(2\rightarrow3)$-galactose, mannose-$\alpha$-$(1\rightarrow2)$-mannose or digalactoside (the $\alpha$-D-Galp-$(1\rightarrow4)$-$\beta$-D-Galp moiety present in the globoseries of glycolipids which in the present context is occasionally termed the globoside).

In many pathogenic bacteria, the adhesin polypeptide proper is believed to form only part of a larger sequence of polypeptides which are all, in one way or another, related to the adhesion function (e.g. polypeptides which mediate the transport of the adhesin through the cell wall or anchor it to the outer surface of the cell wall and so on), and in accordance with the aim of the present invention, a specific adhesin polypeptide is identified among the other polypeptides of the sequence and used as an antigen. This is thought to constitute a less selective identification marker so that antibodies will not only be raised against the strain from which the antigen is derived but also against the other pathogenic strains of the same bacterial species.

Accordingly, the present invention relates to an antigen which, as its major immunizing component, comprises a determinant of an adhesin polypeptide or an immunogenically active subsequence thereof or a precursor therefor which is convertible to an immunologically active form, antibodies against which determinant react with the adhesin polypeptide produced by pathogenic adhesin-forming bacteria which adhere to mammalian tissue. This antigen may comprise an amino acid sequence of at least 5 amino acids and up to the entire amino acid sequence of the adhesin polypeptide.

The adhesin polypeptide may conveniently be derived from adhesin-forming bacteria. This group of bacteria comprises both grampositive and gramnegative bacteria, and the bacterial species of the greatest interest in the present context from which it would be advantageous to derive one or more specific adhesin polypeptides are uropathogenic or enteropathogenic strains of *Escherichia coli* or other enteric bacteria or oral bacteria, *Neisseria gonorrhoeae*, *Neisseria meningiditis*, *Neisseria catarrhallis*, Yersinia spp., *Pseudomonas aeruginosa* or other Pseudomonas spp., *Moraxella bovis* or other Moraxella spp., *Bacteroides nodosus*, Staphylococcus spp., Streptococcus spp. or Bordetella spp. such as *Bordetella pertussis*.

Alternatively, the adhesin polypeptide may be prepared synthetically, as described below.

For some pathogenic bacteria in this group, there is evidence that filamentous structures termed pili (fimbriae) projecting from the cell wall are in some way connected with adhesion, and therefore—and because the pili are easily purified—whole pili preparations have been used as antigens in vaccines, e.g. gonococcus pili antigen (tested in US Army field tests).

Previous investigators working with pili preparations went to great lengths in attemps to prepare "pure" pili protein for protein characterization and immunization, and their efforts were apparently successful in that their preparations only showed one band in SDS gels, (U.S. Pat. No. 4,443,431 (Buchanan T. M. et al); Saliet I. E. & E. C., Gottlisch, *J. Exp. Med.* 146, 1977, p. 1169; Klemm P., I. Orskov & F. Orskov, *Infect. and Immunity* 36, 1982, p. 462; Schoolnik G. K. et al, *J. Exp. Med.* 159, 1984, p. 1351; Svanborg E. C., *Prog. Allergy* 33, 1983, p. 189). The obtained pili protein preparations exhibited at least three functions. The first function was the ability to form polymers, presumably through hydrophobic binding processes; a property essential for the formation of a pilus filament from monomeric subunits. The second property was the ability to engender antibodies; a property which would be essential for any attempts to use the protein as a vaccine. The third property was the ability to adhere to cell surface receptors. Since the investigators were not able to identify more than one protein in their pili protein preparations as well as in the pili themselves, it was concluded that the pili were polymeric aggregates of identical monomeric protein subunits, each subunit having all three of the above-described functions, (U.S. Pat. No. 4,443,431 (Buchanan T. M. et al); Rothbard J. B., *PNAS* 82, 1985, p. 915). However, as mentioned previously, the intact whole pili from a single species has great antigenic diversity. In addition, it has been demonstrated that when used as a vaccine, intact whole pili of a single antigenic type produce antibody primarily to that single antigenic type rather than shared pili antigens. Previous investigators have chemically cleaved the purified pilus subunit into fragments with the proposed functions: Polymerization function, common antigen function, and binding function. Each individual function was identified with a separate fragment of the purified pilus subunit. Thus, it has been assumed that purified pili protein preparations contain a single protein—the pilin monomer. This pilin monomer has been chemically cleaved and assumed to contain the binding function and the principal antigenisity—the same as the polymerized pure pilus protein.

Extensive studies carried out by the applicants demonstrate, however, that the supposed pure pili protein in fact consists of several protein fractions with separate functions. In fact, the pilus filament is not responsible for the cell surface binding but a minor component considered to be a contaminant which is most likely associated with the filament is what is responsible for the cell surface binding. This unique observation could only be ascribed to the fact that the structural formation of pili and the property of adhesion to digalactoside receptors can be genetically dissociated. Other mutated organisms retaining recognizable pili structures but being unable to adhere further confirmed the observation. The implication of the observation was further that the pilus protein, previously supposed to be pure, must contain at least two fractions, one of which is a structural element involved in the actual formation of pili and the other one being a fraction responsible for the adhesion property. The fact that both fractions have antigenic properties opened up the possibility of engendering antibodies against only the adhesion-responsible fraction.

In the case of pilus-carrying bacteria, too, it is advantageous to produce an antigen showing less strain selectivity, if any, and such an antigen is provided by identifying and producing one or more components which form part of the structure of the entire pilus and which mediate the adhesion capacity specifically. In the present context, such a component is termed a pilus adhesin polypeptide. In accordance with what is stated above, the pilus adhesin polypeptide usually comprises a minor component of the entire pilus amino acid sequence of pili derived from pathogenic pilus-forming bacteria and is distinct from the pilin (the subunit of the purified pilus, forming the major part of the pilus fibre). Examples of pilus-forming bacteria which are useful for this purpose are uropathogenic or enteropathogenic strains of *Escherichia coli, Neisseria gonorrhoeae, Neisseria meningiditis, Neisseria catarrhalis, Moraxella bovis* or other Moraxella spp. and *Bordetella pertussis*.

For the purposes of the present invention, the investigations disclosed herein have primarily been concerned with a uropathogenic strain of *E. coli* which gives rise to pyelonephritis. It should, however, be understood that the different *E. coli* genetic systems coding for pilus adhesins are very similar, and that consequently, it is highly probable that such minor pilus components mediating adhesion exist for all types of pilus, i.e. also for pili from other bacteria than *E. coli*. The receptor responsible for the binding of the pathogenic pilus-forming bacteria due to the interlocking structures of the receptor—or part of the receptor—and adhesin molecules, respectively, has been identified for uropathogenic *E. coli* to be the digalactoside, the α-D-Galp-(1→4)-β-D-Galp moiety present in the globoseries of glycolipids, to which the bacteria may attach in the uroepithelium and which is also present on human erythrocytes as a part of the P bloodgroup antigens.

In the course of the research leading to the present invention, the inventors have identified the region on the chromosome of a uropathogenic *E. coli* strain which encodes Pap pili (pili associated with pyelonephritis) which is a 8.5 kb long region which has been found to code for at least eight different polypeptides. The present inventors have also established the polypeptides the absence of which gives rise to non-adhesion of the *E. coli* cells. These polypeptides are therefore assumed to be responsible for the adhesion phenotype of uropathogenic *E. coli*. Consequently, the present invention also concerns an antigen of the amino acid sequence:

Met-Lys-Lys-Ile-Arg-Gly-Leu-Cys-Leu-Pro-Val-Met-Leu-Gly-Ala-Val-Leu-Met-Ser-Gln-His-Val-His-Ala-Val-Asp-Asn-Leu-Thr-Phe-Arg-Gly-Lys-Leu-Ile-Ile-Pro-Ala-Cys-Thr-Val-Ser-Asn-Thr-Thr-Val-Asp-Trp-Gln-Asp-Val-Glu-Ile-Gln-Thr-Leu-Ser-Gln-Asn-Gly-His-Glu-Lys-Glu Phe-Thr-Val-Asn-Met-Arg-Cys-Pro-Tyr-Asn-Leu-Gly-Thr-Met-Lys-Val-Thr-Ile-Thr-Ala-Thr-Asn-Thr-Tyr-Asn-Asn-Ala-Ile-Leu-Val-Gln-Asn-Thr-Ser-Asn-Thr-Ser-Ser-Asp-Gly-Leu-Leu-Val-Tyr-Leu-Tyr-Asn-Ser-Asn-Ala-Gly-Asn-Ile-Gly-Thr-Ala-Ile-Thr-Leu-Gly-Thr-Pro-Phe-Thr  Pro-Gly-Lys-Ile-Thr-Gly-Asn-Asn-Ala-Asp-Lys-Thr-Ile-Ser-Leu-His-Ala-Lys-Leu-Gly-Tyr-Lys-Gly-Asn-Met-Gln-Asn-Leu-Ile-Ala-Gly-Pro-Phe-Ser-Ala-Thr-Ala-Thr-Leu-Val-Ala-Ser-Tyr-Ser or any immunogenically active subsequence thereof, or Met-Ile-Arg-Leu-Ser-Leu-Phe-Ile-Ser-Leu-Leu-Leu-Thr-Ser-Val-Ala-Val-Leu-Ala-Asp-Val-Gln-Ile-Asn-Ile-Arg-Gly-Asn-Val-Tyr-Ile-Pro-Pro-Cys-Thr-Ile-Asn-Asn-Gly-Gln-Asn-Ile-Val-Val-Asp-Phe-Gly-Asn-Ile-Asn-Pro-Glu-His-Val-Asp-Asn-Ser-Arg-Gly-Glu-Val-Thr-Lys-Thr  Ile-Ser-Ile-Ser-Cys-Pro-Tyr-Lys-Ser-Gly-Ser-Leu-Trp-Ile-Lys-Val-Thr-Gly-Asn-Thr-Met-Gly-Gly-Gly-Gln-Asn-Asn-Val-Leu-Ala-Thr-Asn-Ile-Thr-His-Phe-Gly-Ile-Ala-Leu-Tyr-Gln-Gly-Lys-Gly-Met-Ser-Thr-Pro-Leu-Ile-Leu-Gly-Asn-Gly-Ser-Gly-Asn-Gly-Tyr-Gly-Val-Thr-Ala Gly-Leu-Asp-Thr-Ala-Arg-Ser-Thr-Phe-Thr-Phe-Thr-Ser-Val-Pro-Phe-Arg-Asn-Gly-Ser-Gly-Ile-Leu-Asn-Gly-Gly-Asp-Phe-Gln-Thr-Thr-Ala-Ser-Met-Ser-Met-Ile-Tyr-Asn or any immunogenically active subsequence thereof, or Met-Lys-Lys-Trp-Phe-Pro-Ala-Phe-Leu-Phe-Leu-Ser-Leu-Ser-Gly-Gly-Asn-Asp-Ala-Leu-Ala-Gly-Trp-His-Asn-Val-Met-Phe-Tyr-Ala-Phe-Asn-Asp-Tyr-Leu-Thr-Thr-Asn-Ala-Gly-Asn-Val-Lys-Val-Ile-Asp-Gln-Pro-Gln-Leu-Tyr-Ile-Pro-Trp-Asn-Thr-Gly-Ser-Ala-Thr-Ala-Thr-Tyr-Tyr  Ser-Cys-Ser-Gly-Pro-Glu-Phe-Ala-Ser-Gly-Val-Tyr-Phe-Gln-Glu-Tyr-Leu-Ala-Trp-Met-Val-Val-Pro-Lys-His-Val-Tyr-Thr-Asn-Glu-Gly-Phe-Asn-Ile-Phe-Leu-Asp-Val-Gln-Ser-Lys-Tyr-Gly-Trp-Ser-Met-Glu-Asn-Glu-Asn-Asp-Lys-Asp-Phe-Tyr-Phe-Phe-Val-Asn-Gly-Tyr-Glu-Trp-Asp Thr-Trp-Thr-Asn-Asn-Gly-Ala-Arg-Ile-Cys-Phe-Tyr-Pro-Gly-Asn-Met-Lys-Gln-Leu-Asn-Asn-Lys-Phe-Asn-Asp-Leu-Val-Phe-Arg-Val-Leu-Leu-Pro-Val-Asp-Leu-Pro-Lys-Gly-His-Tyr-Asn-Phe-Pro-Val-Arg-Tyr-Ile-Arg-Gly-Ile-Gln-His-His-Tyr-Tyr-Asp-Leu-Trp-Gln-Asp-His-Tyr-Lys  Met-Pro-Tyr-Asp-Gln-Ile-Lys-Gln-Leu-Pro-Ala-Thr-Asn-Thr-Leu-Met-Leu-Ser-Phe-Asp-Asn-Val-Gly-Gly-Cys-Gln-Pro-Ser-Thr-Gln-Val-Leu-Asn-Ile-Asp-His-Gly-Ser-Ile-Val-Ile-Asp-Arg-Ala-Asn-Gly-Asn-Ile-Ala-Ser-Gln-Thr-Leu-Ser-Ile-Tyr-Cys-Asp-Val-Pro-Val-Ser-Lys-Ile  Ser-Leu-Leu-Arg-Asn-Thr-Pro-Pro-Ile-Tyr-Asn-Asn-Asn-Lys-Phe-Ser-Val-Gly-Leu-Gly-Asn-Gly-Trp-Asp-Ser-Ile-Ile-Ser-Leu-Asp-Gly-Val-Glu-Gln-Ser-Glu-Glu-Ile-Leu-Arg-Trp-Tyr-Thr-Ala-Gly-Ser-Lys-Thr-Val-Lys-Ile-Glu-Ser-Arg-Leu-Tyr-Gly-Glu-Glu-Gly-Lys-Arg-Lys-Pro Gly-Glu-Leu-Ser-Gly-Ser-Met-Thr-Met-Val-Leu-Ser-Phe-Pro or any immunogenically active subsequence thereof.

These amino acid sequences have been established by well-known methods as described in Example 5.

The absence of the latter two antigens have been positively demonstrated to cause lack of binding to the globoside receptor in all cases (cf. Example 3 below) and both of these are therefore assumed to be an adhesin polypeptide proper, while the former antigen has been shown to cause lack of binding in certain circumstances only (cf. Example 3 below) and is therefore assumed to be required for anchoring the adhesin polypeptide formed to the outer surface of the cell wall.

It should be noted that the amino acid sequences shown above are the precursor forms of the pilus adhesin polypeptides containing N-terminal signal peptide-like sequences which are cleaved off when the polypeptide is exported through the bacterial inner membrane.

In accordance with the principles of the invention, it is preferred that the antigen of the invention be substantially free from other components related to the adhesion function such as other components of the pilus in order to avoid the formation of a wide variety of antibodies when the antigen is used for immunization with the consequent disadvantages outlined above. Most preferably, the antigen is in substantially pure form, i.e. also free from other determinants which are not in any way connected with adhesin formation but which might give rise to undesirable immunological reactions.

In another aspect, the invention relates to an antibody raised against, or directed substantially only against, an antigen as specified above which, as its major immunizing component, comprises a determinant of an adhesin polypeptide or an immunogenically active subsequence thereof or a precursor therefor which is convertible to an immunologically active form. Such an antibody may be one which is obtained by immunizing an immunizable animal with an antigen as defined above and obtaining antiserum such as immunoglobulins from the animal in a manner known per se. The immunization is preferably performed by means of a stabilized aqueous solution of the antigen; the stabilization agent may be a buffer such as phosphate buffered saline or an adjuvant (also to further increase the antigenicity), and a suitable adjuvant is Freund's adjuvant or aluminium hydroxide. For immunization purposes, mice, rabbits, goats and sheep are the preferred animals, although pig immunoglobulins may also be employed as antibodies. The bleeding of the animal and the isolation of the antiserum is performed according to well-known methods.

The antibody according to the invention is preferably also in substantially pure form which makes it useful for diagnostic purposes as described below.

Alternatively, the antibody may also be produced by a hybridoma technique which is a well-known method for producing antibodies. In the hybridoma technique using for instance mice as the animals immunized, mice are immunized with the antigen in question and spleen cells from the immunized mice are fused with myeloma cells whereupon the fused hybridoma cells are cloned, antibody-producing cells are grown in a suitable growth medium and the antibodies are recovered from the culture. The antibodies obtained by the hybridoma technique have the advantage of greater specificity and hence, greater accuracy of e.g. diagnosis. In a possible further step, using recombinant DNA techniques, the gene or genes encoding the antibody are transferred from the hybridoma cell clone to a suitable vector, the hybrid vector is transformed to a suitable bacterial host, the host is grown in an appropriate medium and the resulting antibody is recovered from the culture. In this way, an improved yield of antibody may be obtained. The host may be one usually employed in the field of recombinant DNA technology such as *Escherichia coli* or *Bacillus subtilis*.

A very important aspect of the present invention concerns a vaccine for immunizing a mammalian subject against diseases caused by pathogenic bacteria which adhere to mammalian tissue, which contains an immunogenically effective amount of an antigen as described above, optionally bound to a suitable carrier, together with an immunologically acceptable vehicle. This vehicle may be any vehicle usually employed in the preparation of vaccines, such as a diluent, suspending agent, adjuvant, etc.

In some cases, it will not be necessary to use a carrier as the antigen tends to polymerize with itself, but in instances where this is not the case, it may be advantageous to bind the antigen covalently to a carrier. This carrier will usually be a polymeric carrier and—especially when the vaccine is to be used to immunize human beings—it is important that it be physiologically acceptable. Synthetic non-toxic and/or non-allergenic carriers for the immobilization of antigens are known, e.g. from Arnon, *J. Immunological Methods* 61, 1983, pp. 261–273. Carriers of this type which are at present contemplated to be useful for this purpose are for instance poly-L-lysine and poly-D,L-alanine. A natural carrier may also be employed provided that it is non-toxic and non-allergenic.

The invention further relates to a method of preparing such a vaccine in which an immunogenically effective amount of an antigen as defined above, optionally bound to a suitable carrier, is combined, e.g. mixed, with an immunologically acceptable vehicle in an amount giving the desired concentration of the antigen in the vaccine preparation.

In a particular embodiment of the method of the invention, an immunogenically active amino acid sequence comprising at least 5 amino acids is covalently bound to the physiologically acceptable carrier, such as one of those mentioned above. The techniques for preparing fused polypeptides are known, e.g. from Casadaban et al., *Methods in Enzymology* 100, 1983, pp. 293–308.

In another embodiment of the method of the invention, the nucleotide sequence encoding an antigen as defined above is fused to the nucleotide sequence encoding a physiologically acceptable carrier polypeptide, the fused DNA sequence is inserted into a suitable vector, the hybrid vector is transformed to a suitable bacterial host, the host is grown in an appropriate medium, and the fused polypeptide is recovered from the culture and optionally purified.

In a further aspect, the invention relates to a DNA fragment which comprises at least the nucleotide sequence encoding an antigen as defined above. It is preferred that the DNA fragment is one which encodes substantially no other antigen. This nucleotide sequence may be one which encodes the entire adhesin polypeptide or which encodes a precursor of an adhesin polypeptide which is convertible to an immunogenically active form or which encodes an immunogenically active subsequence of an adhesin polypeptide. In order to code for an amino acid sequence with immunogenic activity, the DNA fragment should have a length of at least 5 codons (triplets). This DNA may be part of the genetic information residing on the chromosome of or on a plasmid from pathogenic adhesin-forming bacteria, representative examples of which are uropathogenic or enteropathogenic strains of *Escherichia coli* or other enteric bacteria or oral bacteria, *Nesisseria gonorrhoeae, Neisseria meningiditis, Neisseria catarrhalis,* Yersinia spp., *Pseudomonas aeruginosa* or other Pseudomonas spp., *Moraxella bovis* or other Moraxella spp., *Bacteroides nodosus,* Staphylococcus spp., Streptococcus spp. or Bordetella spp. such as *Brodetella pertussls.*

Thus, the DNA fragment may be the DNA or part of the DNA sequence coding for a pilus adhesin polypeptide which may be derived from a pathogenic pilus-forming bacterium, such as a uropathogenic or enteropathogenic strain of *Escherichia coli, Neisseria gonorrhoeae, Neisseria meningiditis, Neisseria catarrhalis, Moraxella bovis* or other Moraxella spp., or *Bordetella pertussis.*

For the purpose of exemplification, the DNA fragment may be one which completely or partially comprises the DNA sequence coding for one or more of the adhesin polypeptides from a uropathogenic strain of *E. coli.* Consequently, the present invention relates to a DNA fragment which—as its major element—is composed of the following DNA sequence:

ATGAAAAAGATAAGAGGTTTGTGTCTTCCGGTAATGCTGGGGGCAGTGTTAATGTCTCAGCATGTACATGCAGTTGATAATCTGACCTTCAGAGGAAAACTGATTATTCCTGCCTGTACTGTAAGCAACACAACTGTTGACTGGCAGGATGTAGAGATTCAGACCCTGAGTCAAAATGGAAATCACGAAAAGAGTTTACTGTGAATATGCGGTGTCCCTATAATCTGGAACAATGAAGGTTACGATAACGGCACAAACACTTATAACAATGCTATTTTAGTTCAGAATACATCAAACACATCTTCTGATGGGTTACTCGTTTATCTTTATAACAGTAATGCAGGAAATATTGGGACTGCGATAACTTTAGGGACTCCATTTACGCCCGGAAAAATCACAGGTAATAATGCAGATAAAACTATATCACTTCATGCCAAACTTGGATATQAAGGGAATATGCAGAATTTGATAGCCGGTCCTTTCTCTGCAACAGCAACGCTGGTTGCAT ATATTCGTAA, or

ATGATTCGTTTATCATTATTTATATCGTTGCTTCTGACATCGGTCGCTGTACTGGCTGATGTGCAGATTAACATCAGGGGGAATGTTTATATCCCCCCATGCACCATTAATAACGGGCAGAATATTGTTGTTGATTTTGGGAATATTAATCCTGAGCACGTGGACAACTCACGTGGTGAAGTCACAAAAACCATAAGCATATCCTGTCCGTATAAGAGTGGCTCTCTCTGGATAAAAGTTACGGGAAATACTATG GAGGAGGTCAGAATAATGTACTGGCAACAAATATAACTCATTTTGGTATAGCGCTGTATCAGGGAAAAGGAATGTCAACACCTTATATTAGGTAATGGTTCAGGAAATGGTTACGGAGTGACAGCAGGTCTGGACACAGCACGTTCAACGTTCACCTTTACTTCAGTGCCCTTTCGTAATGGCAGCGGGATACTGAATGGCGGGGATTTCCAGACCACGGCCAGTATGAGCATGATTTATAACTGA, or

ATGAAAAAATGGTTCCCTGCTTTTTTATTTTTATCCCTGTCAGGCGGTAATGATGCTTTAGCTGGATGGCACAATGTCATGTTTTATGCTTTTAACGACTATTTAACTACAAATGCTGGTAATGTTAAGGTTATTGACCAACCTCAGCTATATATACCCTGGAATACAGGCTCTGCTACAGCAACTTATTATCGTGCTCAGGTCCGGAATTTGCGAGTGGAGTGTATTTTCAGGAGTATCTGGCCTGGATGGTTG TCCTAAACATGTCTATACTAATGAGGGGTTTAATATATTTCTTGATGTTCAGAGCAAATATGGTTGGTCTATGGAGAATGAAAATGACAAAGATTTTTACTTCTTTGTTAATGGTTATGAATGGATACATGGACAAATAATGGTGCCCGTATATGTTTCTATCCTGGAAATATGAAGCAGTTGAACAATAAATTTAATGATTTAGTATTCAGGGTTCTTTTGCCAGTAGATCTCCCCAAGGGACATTATAATTTCCTGTGAGATATATCGTGGAATACAGCACCATTACTATGATCTCTGGCAGGATCATTATAAAATGCCTTACGATCAGATTAAGCAGCTACCTGCCACTAATACATTGATGTTATCATTCGATAATGTTGGGGGATGCCAGCCGTCAACACAAGTACTTAATATAGACCATGGGAGTATTGTGATTGATCGTGCTAACGGAAATATTGCAAGTCAGACGCTTTCAATTTATTGCGATGTACCAGTTAGTGTAAAATTCTCTGCTCAGAAATACACCACCAATATACAATAATAATAAATTTTCGGTTGGGTTAGGTAATGGCTGGGATTCGATAATATCTCTTGATGGGGTTGAACGAGTGAGGAAATATTACGCTGGTACACAGCCGGCTCAAAAACAGTAAAGATTGAGAGCAGGTTGTATGGTGAAGAGGGAAAGAGAAAACCCGGGGAGCTATCTTGGTTCTATGACTAGTGTTCTGAGTTTCCCCTGA or any subsequence thereof which, when expressed, constitutes an immunogenically active subsequence of the adhesin polypeptide encoded by any one of the entire DNA sequence shown above.

The sequence of the respective DNA fragments has been established by well-known methods as described in Example 4.

In a further, important aspect, the invention relates to a method of preparing an antigen comprising, as its major immunizing component, a determinant of an adhesin polypeptide, in which a bacterial host harbouring a hybrid vector containing an inserted DNA fragment which comprises at least the nucleotide type sequence encoding an antigen as defined above, the DNA fragment encoding substantially no other antigen, is cultivated, and the product expressed from the DNA fragment is recovered, optionally followed by purification.

The DNA fragment which encodes an adhesin polypeptide or an immunogenically active subsequence thereof or a precursor therefor which is convertible to an immunologically active form may be obtained, e.g., by excising the same from the bacterial DNA in which it occurs in nature by recombinant DNA technology, e.g. as follows:

Chromosomal DNA from an adhesin-polypeptide generating bacterium is cut up using restriction endonuclease, and the individual DNA fragments are religated with suitable vectors which are then transformed to suitable bacterial hosts. Clones of bacteria that have received the vector are then examined with respect to their adhesin function as assessed by their ability to bind to any solid surface containing the specific receptor, for example by agglutination test with erthrocytes by standard methods. The DNA fragments from the clones which have retained the adhesin function are then subcloned in a suitable vector and then subjected to transposon mutagenesis and/or partial digestion and religation, thereby establishing subclones which contain the smallest DNA fragments which retain the capability of encoding the adhesin function in the bacterial host. Hereby one obtains the smallest necessary piece of DNA operon to express the cell surface adhesin function. Further, manipulations by either transposon mutagenesis or deletion utilizing recombinant DNA technology is used to identify individual genes within the opeon which retain or do not retain the capability of expressing the adhesin polypeptide. Gene or genes expressing adhesin polypeptide are then inserted in a suitable vector, optionally with insertion of suitable promotors to enhance the expression of the adhesin polypeptide or polypeptides. Then, the vector is transformed into a suitable host organism, such as a bacterium, e.g. a gramnegative bacterium such as *E. coli* or *B. subtillis*. Another strategy in the last stage is to selectively block or eliminate genes not essential to the adhesin polypeptide production, in the case of *E. coli*, the papA and papC genes in the above-mentioned smallest necessary piece of DNA operon.

As purification by classical chemical methods of the minor pilus adhesin polypeptide from a preparation in which it is present in admixture with the major pilus structural component (which is normally produced from the same operon) is extremely difficult, if not impossible, due to the fact that the structural component, which is immunogenic per se, is present in much larger amount, this recombinant DNA technique for producing the minor pilus adhesin polypeptide is of decisive importance to obtain an immunogenically effective and sufficiently pure antigen for the purposes of the present invention, as the recombinant DNA technique permits the selective removal of genes encoding undesired antigens, or expressed in another manner, permits selection of the gene or genes encoding the desired minor adhesin polypeptides. By inserting this gene or these genes in suitable vectors, optionally fused with other genes as described herein, it is possible to obtain large amounts of the minor pilus adhesin polypeptides which are otherwise present only in immunogenically substantially ineffective, hitherto neglected small proportions in the known pilus preparations.

In accordance with a special embodiment, several genes encoding one or several of the desired adhesin polypeptides may be inserted in the same vector, so that the resulting product produced by the microorganism will be a product with recurring determinants of the antigen in question, thus enhancing the immunogenity or receptor-binding efficiency.

All of these operations are carried out in accordance with methods well known in the field of recombinant DNA technology and explained in more detail in Examples 1-3 below. The vector used in this method may be any vector usually employed for the purpose such as pBR322 derivatives, lacUV5 promoter vectors, broad host range vectors such as Tac promoter vectors, shuttle vectors, runaway plasmid derivatives, etc. The growth medium in which the bacterial host is grown may be any growth medium conventionally employed for fermentation processes such as e.g. L-broth or M9 glycerol medium. The bacterial host is conveniently selected among hosts whose behaviour under fermentation conditions is known, such as *Escherichia coli* or *Bacillus subtillis*.

Purification which, as mentioned above, will be advantageous in many cases as the formation of irrelevant antibodies, i.e. antibodies which take no part in the immunization against the antigen in question, and which may even give rise to undesirable reactions on the part of the animal in which it is formed, is avoided as is the administration concurrently with the antigen of possible toxic substances formed by the host bacterium, e.g. a lipopolysaccharide, has, however, been found to be problematic. In order to facilitate purification, a method has been devised involving the use of fused polypeptides. In this method, a DNA fragment encoding a first polypeptide comprising the adhesin polypeptide or an immunogenically active subsequence thereof or a precursor therefor which is convertible to an immunologically active form is fused to a DNA sequence encoding a second polypeptide, the fused DNA sequence is inserted into a suitable bacterial host, the host is grown in an appropriate medium, the fused polypeptide is recovered from the culture and purified using an assay involving antibodies raised against the second polypeptide, and the second polypeptide is optically cleaved off by means of a suitable protease followed by separation of the two polypeptides.

An example of a DNA sequence which may advantageously be employed for this purpose is the lacZ gene encoding $\beta$-galactosidase, as the expression of this gene product and consequently of the adhesin polypeptide or subsequence thereof or precursor therefor is easy to detect, e.g. by growing the bacterial host or lactose indicator plates and selecting for the positive (Lac+) colonies.

After purification, the second polypeptide may be cleaved off by means of a protease such as trypsin or chymotrypsin. Desired peptide fragments which only derive from the DNA fragment encoding the first polypeptide to which the gene coding for the second polypeptide has been fused are selected on the basis of their immunogenic activity, e.g. as tested in vitro. Separation of the two polypeptides may be performed by standard methods such as by ion exchange chromatography, HPLC reverse phase chromatography or affinity chromatography such as immunoaffinity chromatography or receptor affinity chromatography. In the case of immunoaffinity chromatography, either the antibodies raised against the antigens of the invention (comprising the first polypeptide) or the antibodies raised against the second polypeptide may be employed as the antibodies immobilized in the column. In receptor affinity chromatography, the receptor for the adhesin produced may be similarly employed. The DNA fragment used for the fusion with the DNA sequence encoding the second polypeptide may be any of the DNA fragments indicated above.

In an alternative method of preparing the antigen of the invention, the adhesin polypeptide such as the pilus adhesin polypeptide or immunogenically active subsequence thereof may be prepared by peptide synthesis according to well-known methods such as by liquid phase peptide synthesis or by solid phase peptide synthesis (cf. for instance Stewart and Young, *Solid Phase Peptide Synthesis*, Freeman & Co., San Francisco, USA, 1969). Solid phase peptide synthesis is the preferred method. In solid phase peptide synthesis, the amino acid sequence is built by coupling an initial amino acid to a carrier and then sequentially adding the other amino acids in the sequence by peptide bonding, in this case to a length of at least 5 amino acids. When preparing the adhesin polypeptide or subsequence thereof by solid phase peptide synthesis, it may therefore be advantageous to use the physiologically acceptable polymer useful as carrier for the antigen in the vaccine as the carrier to which the initial amino acid in the sequence is coupled. The preparation of synthetic peptides for use as vaccines may otherwise be performed essentially as described in Shinnick, "Synthetic peptides, immunogens and vaccines", Ann. Rev. Microbiol. 37, 1983, pp. 425≧446.

According to the invention, the antibody raised against, or directed substantially against, an antigen which comprises a determinant of an adhesin polypeptide or an immunogenically active subsequence thereof or a precursor therefor which is convertible to an immunologically active form may be used in a composition for the passive immunization of a mammalian subject against diseases caused by pathogenic bacteria which adhere to mammalian tissue, which comprises an immunologically effective amount of an antibody as defined above, optionally bound to a suitable carrier, together with an immunologically acceptable vehicle. This composition may be prepared by a method comprising combining an immunogenically effective amount of the antibody with the immunologically acceptable vehicle, e.g. by mixing the components.

The carrier to which the antibody is optionally covalently bound may be any of the carriers mentioned above in connection with the description of the vaccine. The vehicle with which the antibody is mixed may be any vehicle usually employed for this purpose, such as a diluent, suspending agent, adjuvant, etc., added in an amount to give the desired concentration of antibody in the composition.

Though less efficient for immunization than the antigen described above, the antibody may thus be used for immunization purposes, but its principal use is as a diagnostic agent for the diagnosis of infectious diseases caused by pathogenic adhesin-forming bacteria which adhere to mammalian, e.g. human, tissue, examples of which are uropathogenic or enteropathogenic strains of *Escherichia coli* or other enteric bacteria or oral bacteria, *Neisseria gonorrhoeae, Neisseria meningiditis, Neisseria catarrhalis,* Yersinia spp., *Pseudomonas aeruginosa* or other Pseudomonas spp., *Moraxella bovis* or other Moraxella spp., *Bacteroides nodosus,* Staphylococcus spp. Streptococcus spp., or Bordetella spp. such as *Bordetella pertussis.* The invention therefore also relates to a diagnostic agent which comprises an antibody as described above, such as an antibody raised against an immunogenic determinant of a pilus adhesin polypeptide, or an antibody raised against an immunogenic determinant of an antigen which is not an adhesin polypeptide or a subsequence thereof or precursor therefor. This antigen may for instance be another polypeptide encoded by an adhesin gene cluster (a sequence of genes which are somehow involved in mediating the adhesion capacity of the bacteria carrying them), for instance one of the other polypeptides involved in the formation of pili, in the case of the pilus polypeptides from uropathogenic *E. coli,* e.g. the gene products of the genes papB, papC or papD (as shown in FIG. 1 and/or FIG. 2) encoding polypeptides of 13 kd, 81 kd and 28.5 kd, respectively. The papC and papD gene products are at present believed to mediate the assembly and/or anchorage of pilin subunits (encoded by the gene papA) during the pilin secretion and polymerization process (for the formation of pili).

When used as diagnostic agents, the antibodies may be labelled with, for instance, a colouring agent so that bacteria containing the antigen to be detected appear as coloured agglomerates in the diagnostic test. Other standard methods such as enzyme-linked immunosorbent assay (ELISA; cf. Materials and Methods) or radioimmunoassay (RIA) using radiolabelled antibodies may also be employed.

Alternatively, the diagnostic agent may comprise a stable, labelled DNA sequence which is at least about 60% homologous with a DNA sequence in the bacterium whose presence or absence is to be established by the diagnostic test. In the present context, the term "stable" is intended to indicate that the nucleotide sequence is relatively constant, i.e. that base pair substituents in which one base pair is replaced by another are reasonably infrequent. In many genes, such base pair substitutions are relatively common without necessarily affecting the amino acid composition of the gene products which are expressed from them, but the base pair substitutions affect the diagnostic process which relies on a fairly high degree of homology between the DNA from the probe and the bacterial DNA used as the specimen to be tested, as the DNA (sub)sequence of the probe recognizes the same sequence or one which resembles it rather closely in the bacterial DNA. In the diagnostic process, probe DNA is labelled, and the DNA is denatured to separate the strands in both the probe and the bacterial DNA; after mixing the DNAs, the strands are left to reform the double helical structure, but in case of homology (DNA sequence recognition), some of the probe DNA will have been introduced in the bacterial DNA. This technique is known as hybridization and is described in e.g. Southern, *Methods in Enzymology* 68, 1980, pp. 151-176. In order to have sufficient specificity as a diagnostic agent, the DNA used as the probe should comprise a unique nucleotide sequence and should therefore have a length of at least 12 nucleotides. The probe DNA may advantageously be labelled with a radioactive isotope such as $^3$H or $^{14}$C in a manner known per se.

The DNA sequence used as probe DNA may be one which comprises a gene which is part of an adhesin gene cluster, but which does not encode the adhesin polypeptide itself, or a diagnostically effective subsequence therof. This gene may, for instance, be one which codes for a pilus polypeptide produced by a pathogenic pilus-forming bacterium which is not a pilus adhesin polypeptide, or a diagnostically effective subsequence thereof. In the system exemplified herein, the DNA sequence encoding the pilus polypeptide or a subsequence thereof is derived from a uropathogenic strain of *Escherichia coli.* Particularly advantageous diagnostic agents in this system have been found to be the genes papB, papC and papD—due to their genetic stability as defined above—or a diagnostically effective subsequence of any of those genes.

As described above, the antigen according to the invention may be used as a component of a vaccine. Accordingly, this invention also comprises a method of immunizing a mammal such as a human being against diseases caused by pathogenic bacteria which adhere to mammalian, e.g. human, tissue, which comprises administering a vaccine containing an immunogenically effective amount of an antigen as described above, optionally bound to a suitable carrier, or a composition for passive immunization containing an antibody as described above, also optionally bound to a suitable carrier, and an immunologically acceptable vehicle. The administration may be performed in a manner known per se, such as by injecting the antigen or antibody in admixture with a suitable injection vehicle such as isotonic saline.

These patogenic bacteria may be any bacteria which form adhesins or adhesin-like polypeptides, examples of which are uropathogenic or enteropathogenic strains of *Escherichia coli* or other enteric bacteria or oral bacteria, *Neisseria gonorrhoeae, Neisseria meningiditis, Neisseria catarrhalis*, Yersinia spp., *Pseudomonas aeruginosa* or other Pseudomonas spp., *Moraxella bovis* or other Moraxella spp., *Bacteroides nodosus*, Staphylococcus spp., Streptococcus spp., or Bordetella spp., such as *Bordetella pertussis*. An interesting class of such bacteria is constituted by pilus-forming bacteria, important examples of which are uropathogenic or enteropathogenic strains of of *Escherichia coli, Neisseria gonorrhoeae, Neisseria meningiditis, Neisseria catarrhalis, Moraxella bovis* or other Moraxella spp., or *Bordetella pertussis*.

Finally, it is contemplated that the antigen according to the present invention may be employed to determine the presence of the receptor for the particular adhesin polypeptide or active part thereof on mammalian tissue cells such as epithelial cells. This is of potential importance for identifying persons belonging to high-risk groups, i.e. persons who appear to be predisposed for certain kinds of infection as such persons are those who produce large amounts of the receptor to which the pathogenic bacteria causing the infection in question bind by means of the adhesins they produce. When such persons have been identified, prophylactic treatment, i.e. principally immunization/vaccination, may be carried out. The method of determining the presence of the adhesin receptor and the amounts of adhesin receptor present may comprise incubating a specimen comprising tissue samples or cell scrapings with the adhesin followed by washing. An antibody raised against the adhesin and labelled with, e.g., fluorescence or a radioactive isotope such as I-125, may be incubated with the specimen, or alternatively the thus labelled adhesin may be used directly in the test. The amount of adhesin receptor in the specimen may then be determined by measuring the amount of radioactivity of fluorescence in the specimen in a manner known per se.

Specifically, it is contemplated that the adhesin polypeptides of a uropathogenic strain of *E. coli*, the amino acid sequences of which are given above, may be used to thus identify women who produce larger amounts of the globoside receptor in their urinary tract and who are therefore assumed to be predisposed for urinary tract infections.

This aspect of the invention can be expressed generally as a method of determining receptor density or distribution in a host mammal such as a human, comprising treating a tissue sample from the host with a receptor-specific polypeptide, removing unbound receptor-specific polypeptide and determining the amount of receptor-specific polypeptide bound. The determination of the amount of polypeptide bound may either be made by labelling the polypeptide or by incubating the specimen with a labelled antibody, such as described above.

This method of the invention is very advantageous compared to previous methods where the receptor density or receptor distribution was determined by means of an antibody which was directed against the specific receptors, the reason being that the reactor-specific polypeptide, exemplified by the adhesin polypeptide, can bind to the specific receptor, whether the receptor itself, which is usually one or two sugars, is at the end of a chain of sugars or whether the system of two sugars is somewhere in the middle of the chain, whereas the antibody will only recognize two sugars at the end of the chain, but not the sugars in the middle. Therefore, the binding repertoire of the antibody is limited as compared with the adhesin polypeptide and any attempt to quantify a receptor density will be always underestimated when using antibody for direct combination with the receptors.

Finally, an aspect of the invention relates to a method for preventing or reducing the possibility of infection of a human being or other mammal with a pathogenic adhesin-binding microorganism, the method comprising treating the human being or other mammal with one or more adhesin polypeptides in a suitable method to distribute the polypeptides over the cell surfaces for which infection with a specific pathogenic bacteria is to be prevented, the adhesin polypeptide used being an adhesin polypeptide that will bind with the receptors with which the adhesin generated by the pathogenic bacteria will bind. In this case the adhesin polypeptide is not used as an antigen, but as a direct preventive therapeutic agent to occupy the receptors, thus making it possible for the pathogenic bacteria to bind to the receptor. In most topical infections, the first step is a specific binding to the specific cell surface of adhesin polypeptide from the specific bacteria, which means that when the receptors are already occupied, the first step in a process to develop an infection cannot take place. With the bacteria being unable to bind, the infection does not occur.

DESCRIPTION OF THE DRAWINGS

The invention is further described with reference to the drawings in which.

Figure 1:
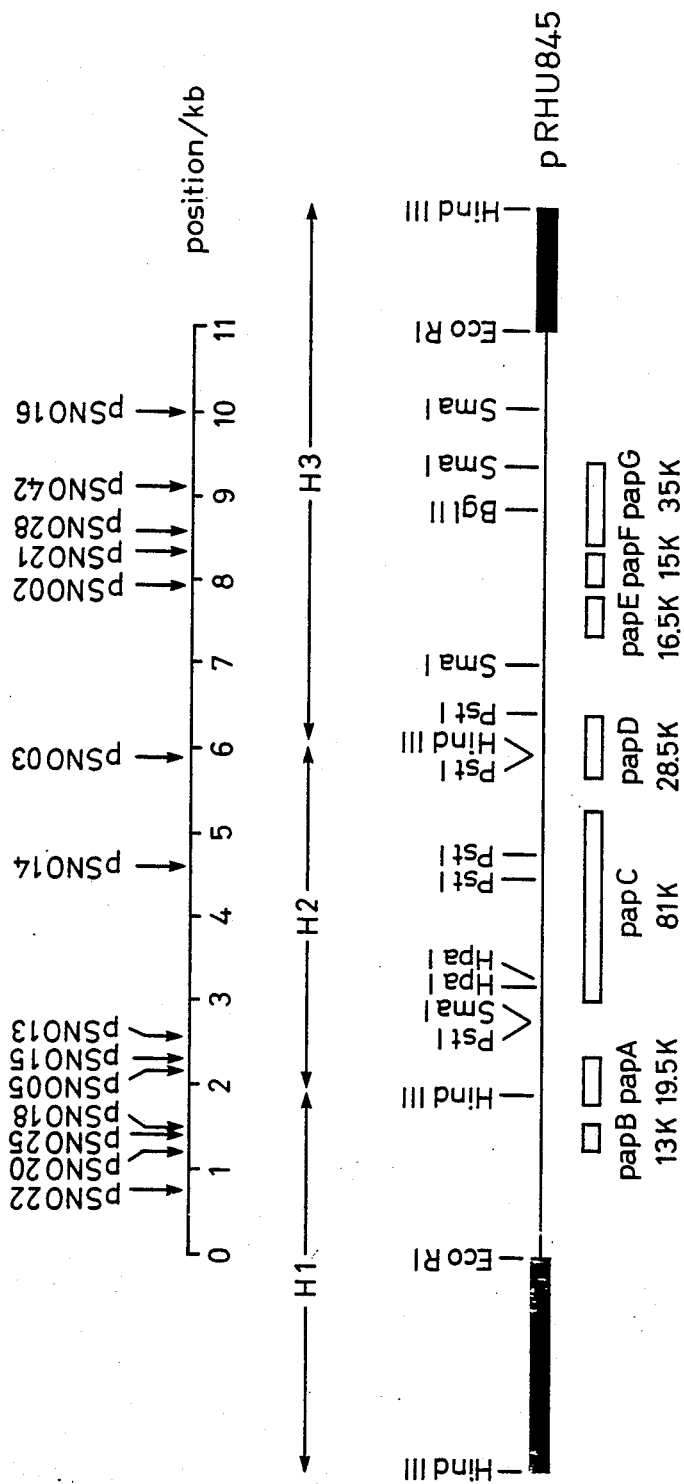
FIG. 1 is a map which shows the genetic organization of Pap DNA in pRHU845. The upper line shows the size (in kilobase pairs) of the EcoRI fragment inserted in plasmid pACYC184. The positions for various Tn5 insertions are given above. The restriction map of pRHU845 and the positions for identified pap genes are given. The thick vertical bar represents the region coding for the signal peptide. The designations under the bars refer to the molecular weights ($\times 10^3$ dalton units) of the mature polypeptides.

The construction and characterization of the plasmids shown in the drawing are described in Materials and Methods as well as in Examples 1-3.

GENERAL MATERIALS AND METHODS

Chemicals and enzymes

Restriction enzymes and T4 DNA ligase were purchased from Boehringer Mannheim GmbH or New England BioLabs, and used as recommended by the manufacturers. Filling in of 3'-recessive ends was performed by using the Klenow fragment (New England BioLabs) in ligation buffer to which 200 μM each of the required dNTPs had been added. The XhoI linker (5'-CCTCGAGG-3') and BamHI linker (5'-CGGATCCG-3') were obtained from Collaborative Research and 5'-phosphorylated as described by the manufacturers using polynucleotide kinase from New England Biolabs. All chemicals were of the highest purity commercially available. p-erythrocytes were kindly supplied by Dr. B. Cedergren, Blood Bank, University Hospital, Umeå.

Purification of pili

Pili were purified according to a modification of the method described by Brinton et al., *Immunobiology of Neisseria gonorrhoeae*, Washington DC, USA, 1978, pp. 155-178. Cells were grown for 22 hours at 37° C. on five trays (400×250 mm) containing L-agar without glucose. The cells were scraped off the trays, suspended in 340 ml ice-cold 5 mM Tris-HCl (pH 8.0) and blended for 10 minutes on ice in a Sorvall Omnimixer at setting 4. After pelletation of the cells and cellular debris (twice for 30 minutes at 20,000×g), ammonium sulfate was added to the supernatant to 55% saturation and pili were allowed to precipitate on ice overnight. The precipitate was collected by centrifugation and resuspended in 5 mM Tris (pH 8.0). After dialysis overnight against the same buffer at 4° C., non-dissolved material was removed by centrifugation for 30 minutes at 40,000×g. The precipitation-dialysis procedure was repeated an additional three times (precipitation for 3 hours) after which pili were precipitated by adding 0.2 volumes of 1M $MgCl_2$-1.5M NaCl-100 mM Tris-HCl (pH 7.5). The precipitate was dissolved in a protein concentration of 2 mg/ml as measured according to Lowry et al., *J. Biol. Chem.* 193, 1951, pp. 920-929. The yield was about 15 mg for the wild-type and 2-30 mg for the mutants.

Receptor binding assays

For slide agglutination, bacterial cells grown for 22 hours on glucose-free L-agar were suspended to about $10^{10}$ cells/ml in agglutination buffer (150 mM NaCl 10 mM Tris-HCl pH 7.5) containing 3% heparinized and washed human erythrocytes. The reaction, when positive, was usually apparent within 60 seconds. The positive reaction was a macroscopically visible aggregation of erythrocytes. In the semiquantititive assay, cells grown as above were resuspended to an $A_{600}=20$. They were then serially 2-fold diluted in 50 μl agglutination buffer using microtiter plates with conical-bottom wells (Linbro/Titertek, cat. no. 76-321-05, CT, USA). To this was added 10 μl of a 3% erythrocyte suspension in the same buffer. The dilution in the last well giving a positive agglutination after 2 hours at 4° C. was taken as the agglutination titer. The cell count of the original suspension was used together with the titer, to calculate the minimum bacterial concentration required for agglutination.

The agglutination titer of purified pili was determined essentially in the same way as that used for whole cells. When using agglutination buffer, however, the pilus concentration required for agglutination was very high and various attempts were made to increase the sensitivity of the assay. Since pili are negatively charged at physiological pH and aggregate in the presence of 167 mM $MgCl_2$ (see Purification of pili), a wild-type pilus preparation was titrated at increasing $MgCl_2$ concentrations, using $P_1$-erythrocytes containing the globoside receptor (including the digalactoside), and p-erythrocytes which lack this carbohydrate. The agglutination titer was found to increase 128-fold when the $MgCl_2$ concentration was increased to 100 mM. This was paralleled by an increase of $A_{400}$ of a 200 μg/ml pilus solution in the same buffers. With $CaCl_2$ and 10-fold higher concentrations of $NH_4Cl$, the same results are obtained, suggesting that the effect is on pilus-pilus interaction and not on specific receptor binding. In addition, the agglutination titer of whole piliated cells is not significantly affected by the addition of $MgCl_2$ up to 200 mM. Also the increase in agglutination titer using p-erythrocytes shows that unspecific pilus-erythrocyte aggregation is favoured by the addition of $Mg^{2+}$ ions, although the specificity of the assay ($P_1$-titer over p-titer) seems to be unaffected. All titrations of pilus preparations were therefore made in agglutination buffer with 100 mM $MgCl_2$ to give a semiquantitative value for specific agglutination.

Antibody production

Preimmune sera were obtained from two healthy 1.8 kg female New Zealand white rabbits by cardiac puncture, filter sterilized and stored at −20° C. 75 μg of purified Pap pili in 1.0 ml of isotonic saline was emulsified with an equal volume of Freund's complete adjuvant and injected in 0.5 ml amounts into four sites, namely subscapularly at two sites and intramuscularly into the two hind legs. After 6 weeks, a booster injection with Freund's complete adjuvant was given. Ten days after the second immunization, the animals were bled by cardiac puncture, and the serum was filter sterilized and stored with 0.02% sodium azide at −20° C.

Pilus antigen assay

For slide agglutination, bacteria was grown and prepared as described for the hemagglutination assays. Agglutination tests of whole cells were performed with 500-fold diluted (PBS pH 7.5) antiserum raised against purified Pap pili (cf. above). The positive reaction was determined as a macroscopically visible aggregation of bacteria which appeared within 60 seconds.

Protein expression in minicells

Plasmid pPAP5 and its derivatives were transformed to the minicell-producing strain P678-54 (Adler et al., *Proc. Natl. Acad. Sci. USA* 57, 1967, pp. 321-326). Preparation and labelling of plasmid-containing minicells with [$^{35}$S]methionine were as described by Thompson and Achtman, *Mol. Gen. Genet.* 165, 1978, pp. 295–304. The radioactive samples were subjected to SDS-polyacrylamide electrophoresis (cf. below). The gels were subsequently fixed, stained, enhanced (Enhance, New England Nuclear) and autoradiographed. Molecular weight standards (Pharmacia Fine Chemicals, Uppsala, Sweden) and purified pilin were electrophoresed in parallel.

SDS-polyacrylamide gel electrophoresis

Radiactive samples were suspended in 100 μl of sampling buffer containing 62.5 mM Tris-HCl (pH 6.8). 1% sodium dodecyl sulfate (SDS), 0.5% β-mercaptoethanol, and 10% glycerol. After 5 minutes of boiling, the extracts were electrophoresed in 15% polyacrylamide slab gels containing 0.1% SDS (Laemmli, *Nature* 227, 1970, pp. 680–685. Protein standards with molecular weights ranging from 3,000 to 94,000 were run in parallel. After fixation, staining and destaining (Grundström et al., *J. Bacteriol.* 143, 1980, pp. 1127–1134), the gel was fluorographed by using En$^{3-}$Hance (New England Nuclear Corp., Boston, Mass.).

Transposon mutagenesis

Transposon mutagenesis with Tn5 was performed essentially as described by Björk and Olsén, *Acta Chem. Scan. Ser. B* 33, 1979, pp. 591–593, with phage λ cI$_{587}$b221 rex::Tn5.

Cell extracts

Cells of strain P678-54 containing various hybrid plasmids were grown on tryptic soy agar in the presence of the appropriate antibiotics. Bacteria were harvested after overnight growth at 37° C. suspended in PBS (pH 7.2)-Brij ®-35 to a cell density of 1.5 absorbance units at 560 nm, and collected by centrifugation (12,000×g for 10 minutes). The cell pellet was next suspended in 400 μl of 1% Nonidet P-40-1% sodium deoxycholate-0.1% SDS-0.15 m NaCl-0.01M Tris-HCl (pH 7.2) containing lysozyme at 1 mg/ml and was incubated for 10 minutes at 4° C. (26). A 400 μl sample of a 1/15,000 dilution of Pap antisera was added to the cell extract. After incubation at 4° C. for 16 hours, the cell extract antibody mixture was clarified by centrifugation (12,000×g for 10 minutes).

Competitive enzyme-linked immunosorbent assay (ELISA)

Disposable microtiter hemagglutination plates (Cooke polystyrene, 96 U wells) were exposed to 100 μl of a 1 μg/ml solution of purified Pap pili per well in 0.1M sodium carbonate buffer (pH 9.6) for 16 hours at 25° C. The wells were washed three times with 0.15M NaCl containing 0.05% (vol/vol) Brij ®-35 (Sigma) to remove unbound pili. Anti-Pap pilus rabbit antiserum was diluted in PBS (pH 7.2) with 0.05% (vol/vol) Brij ®-35 to a concentration which resulted in 50% maximal binding (1/30,000 dilution) and was then mixed with serial dilutions in PBS-Brij ® lysates of whole bacteria, cell-free extracts, or Pap pili (positive control), or without added pili (negative control). After incubation for 16 hours at 4° C., 100 μl samples were transferred to the sensitized microtiter wells. The plates were incubated for 3 hours at 37° C. and were then washed three times with NaCl-Brij ®. Alkaline phosphatase-conjugated goat anti-rabbit immunoglobulin G diluted 1/1,000 in PBS-Brij ® was added to all wells and incubated for 1 hour at 37° C. The plates were washed three times with PBS-Brij ®, and 1 mg of p-nitrophenylphosphate (Sigma) per ml in 1.0M diethanolamine buffer (pH 9.8) was added to each well and incubated for 20 minutes at 37° C. The reaction was stopped by the addition of 2N NaOH, and absorbance at 405 nm was determined with an MR 580 MicroELISA autoreader (Dynatech 011-960-0000; Dynatech Laboratories, Alexanderia, Va.).

Immunoprecipitation

Immunoprecipitation of [$^{35}$S]methionine-labelled, plasmid-encoded proteins was performed essentially as described by Dallas and Falkow, *Nature* 277, 1979, pp. 406–407, with the exception that pure *Staphylococcus aureus* Protein A bound to Sepharose ® was used instead of *Staphylococcus aureus* cells.

Western blotting

Western blotting after SDS-polyacrylamide gel electrophoresis of purified pili was performed as described by Swanson et al., *Infect. Immun.* 38, 1982, pp. 668–672. Diluted Pap antiserum raised against pili purified from strain P678-54 harbouring plasmid pRHU845 (enzyme-linked immune sorbent assay titer, 1:1,000) was used.

Construction of plasmid derivatives

Figure 2:
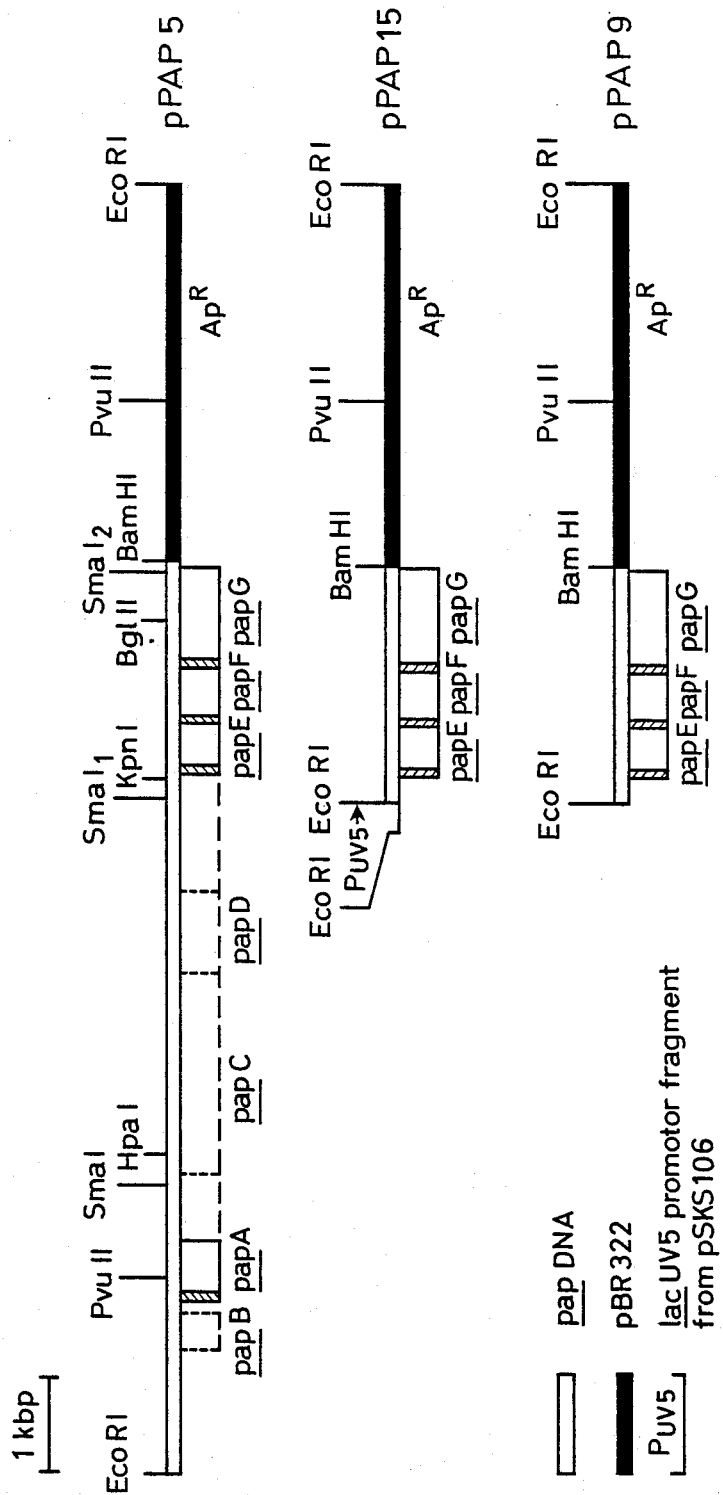
FIG. 2 shows the restriction maps and genetic organization of pap hybride plasmids used for in vitro mutagenesis. Plasmid pPAP5 carries the entire EcoRI-BamHI fragment necessary for expression of Pap pili and digalactoside-specific agglutination of human erythrocytes. Plasmid pPAP16 carries only the SmaI$_1$-BamHI fragment under transcriptional control from the lacUV5 promoter. Plasmid pPAP9 is identical to pPAP16 with the exception that it does not carry the lacUV5 promoter. Below the horizontal line, Ap$^R$ denotes ampicillin resistance (100 µg/ml).

The 9.6 kb long EcoRI-BamHI fragment of pRHU30, containing all the genes necessary for the expression of Pap pili and digalactoside-specific binding, was cloned into EcoRI- and BamHI-digested pBR322 (Bolivar et al., *Gene* 2, 1977, pp. 95–113) giving pPAP5 (cf. FIG. 2). To construct a derivative lacking the PvuII site in the pBR322 part of the molecule, the vector was PvuII digested and ligated to a 20-fold excess of BamHI linker. This DNA was subsequently cut with EcoRI and BamHI, and the largest fragment carrying nucleotides 2065–4360 of pBR322 (Sutcliffe, *DNA: Relication and Recombination* 43, Cold Spring, Harbor Laboratory Press, New York, 1978, pp. 77–90) was isolated from a 0.7% agarose gel. This fragment, ligated to the EcoRI-BamHI from pRHU30, was transformed (Mandel and Higa, *J. Mol. Biol.* 53, 1970, 159–162) into *E. coli* strain HB101 (Boyer and Roulland-Dossoix, *J. Mol. Biol.* 41, 1969, pp. 459–472). The isolated clone was named pPAP22 and is identical to pPAP5 except that the clone lacks the BamHI-PvuII segment. A derivative, pPAP23, carrying a frame-shift mutation at the single PvuII site in papA was constructed by linearizing pPAP22 with PvuII and ligating it to a 20-fold excess of XhoI linker. After digestion for 3 hours using 20 units of XhoI/μg of DNA, the fragment was purified on a Sephadex ® G150 column (Pharmacia Fine Chemicals, Uppsala, Sweden) equilibrated with 10 mM Tris-HCl pH 8.0 and 1 mM EDTA. After ligation and transformation into E. coli strain HB101, DNA from six clones was isolated (Birnboim and Doly, *Nucleic Acids Res.* 7, 1979, pp. 1513–1523) and analyzed. Five of the clones had a new XhoI site at the former PvuII site and one of these was called pPAP23 and used in further studies. The following manipulations were done to construct plasmid pPAP16 (FIG. 2) and derivatives of both this plasmid and pPAP5 with mutations in the SmaI$_1$-BamHI region. Plamid pPAP1 was constructed by linearizing 2 μg of pBR322 with ClaI, and blunt ends were created using 5 units of Klenow fragment and 200 μM each of dGTP and dCTP (15 minutes at 30° C. in ligation buffer). This DNA was, after heat inactivation of the enzyme, ligated to the gel-purified SmaI$_1$-SmaI$_2$ fragment of pPAP5 (FIG. 2), and by screening small-scale plasmid preparations, a plasmid carrying the fragment in the same orientation relative to the vector as on pPAP5, was isolated. The clone pPAP1 expressed the last polypeptide (35 kd) in a slightly truncated form. Thus the gene for this polypeptide extends beyond the SmaI$_2$ site and is present in a truncated form in pPAP1. This mutation was isolated on a KpnI-BamHI fragment which was ligated into pPAP5 cut with these enzymes. The derivative, pPAP7 obtained in this way thus contains pap DNA up to the SmaI$_2$ site. Plasmid pPAP9, containing the whole SmaI$_1$-BamHI region was constructed by ligating the KpnI-BamHI fragment of pPAP5 in excess to KpnI-BamHI digested pPAP1. To make frameshift mutations in the insert of pPAP9, this plasmid was partially digested with HincII in the presence of 150 μg/ml ethidium bromide (Greenfield et al., Biochim. Biophys. Acta 407, 1975, pp. 365-375). Linearized plasmid was then isolated from a 0.7% agarose gel and ligated to an excess of XhoI linkers. After KhoI digestion, Sephadex ® G150 gel chromatography, and ligation, the DNA was transformed into E. coli strain HB101, selecting for ampicilling resistance. The DNA purified from 23 clones was analyzed by digestion with XhoI and SalI. Of 15 mutants within the insert, 13 were linker insertions at HincII$_2$ and two at the HincII$_1$ site. No mutants at HincII$_3$ were obtained. pPAP5 derivatives carrying these mutations were constructed in a way analogous to pPAP7. These plasmids were named pPAP15 (HincII$_1$) and pPAP14 (HincII$_2$). pPAP19 was constructed by deleting the XhoI-SalI fragment of pPAP14 by re-ligating an XhoI-SalI digest of the latter plasmid. The construction of pPAP20 from pPAP15 was done in the same manner. To make plasmid pPAP26 (papA1, papE1 doublet mutant), the large KpnI-BamHI fragment of pPAP23 (papAI) was ligated to the small KpnI-BamHI fragment of pPAP10 (papE1). Plasmid pPAP9 did not complement Tn5 insertions within the SmaI$_1$-BamHI region. This was suspected to be due to insufficient transcription over the insert. Therefore the EcoRI fragment containing the lacUV5 promoter was isolated from pSKS106 (Casabadan et al., Methods Enzymol. 100, 1983, pp. 293-308), and ligated in excess to EcoRI linearized pPAP9. A clone with the fragment in the correct orientation, pPAP16, was subsequently isolated by screening DNA preparations using PstI digestion since the promoter fragment carries an asymmetrically placed site for this enzyme. The same procedure was applied to the other pPAP9 derivatives resulting in pPAP4 (SmaI$_2$-BamHI deletion), pPAP18 (HincII$_1$ mutation) and pPAP17 (HincII$_2$ mutation).

EXAMPLE 1

Cloning and identification of the gene for the major pilus subunit

High molecular weight chromosomal DNA from a spontaneously Lac$^-$ derivative of a uropathogenic isolate of E. coli J96 (cf. R. Hull et al., Infect. Immun. 33, 1981, pp. 933-938; mannose-resistant hemagglutination (MRHA$^+$) and digalactoside-specific binding) was isolated according to standard methods. This DNA was subsequently partially digested with the restriction endonuclease Sau3A. The restriction fragments were ligated to the plasmid vector pHC79 (Collins, Methods Enzymol. 68, 1979, pp. 309-326) which had previously been linearized with the restriction endonuclease BamHI. This DNA was in vitro packaged into λ phage particles according to the procedure described by B. Holm, Methods in Enzymology 68, 1979, pp. 1127-1134. These particles were used to infect E. coli strain P678-54 (Adler et al., op. cit.). The bacteria were then spread on plates containing amplicillin leading to the formation of colonies containing the recombinant plasmid which is ampicillin-resistant.

Individual colonies were screened for agglutination of human erythrocytes in the presence of 1% of mannose, and the clone (pRHU807) causing mannose-resistant hemagglutination was selected. Subclones (pRHU30 and pRHU845) of pRHU807 were constructed retaining MRHA$^+$ as described by R. Hull et al., op. cit. The presence of both of these subclones in E. coli strain HB101 also causes the formation of pili. The hemagglutination caused by E. coli strain HB101 containing pRHU845 was totally inhibited by the presence of soluble digalactoside, both in the presence and in the absence of mannose, thus demonstrating that in this case the MHRA$^+$ phenotype expressed by this strain is identical to digalactoside-specific binding.

The structural gene for the major polypeptide forming the Pap (pili associated with pyelonephritis) pilus (papA) was identified by Western blotting and immunoprecipitation from subclones and mapped to about 2.2 kb as shown in FIG. 1. The position of the papA gene was confirmed by the identity between the amino acid sequence of the gene product inferred from the DNA sequence (M. Båga et al., J. Bacteriol. 157, Jan. 1984, pp. 330-333) comparing it with the N-terminal sequence of the major Pap pilus subunit (cf. O'Hanley et al., J. Exp. Med. 158, Nov. 1983, pp. 1713-1719).

EXAMPLE 2

Identification of the pilus DNA sequence

To characterize the genes required for Pap pilus formation and digalactoside-specific agglutination, subclones of pRHU845 and transposon Tn5 insertion mutants were constructed and analyzed as described in Normark et al., Infect. Immun. 41, Sept. 1983, pp. 942-949. By further analysis of the Tn5 insertion mutants and subclones, it was shown that only the DNA residing between position about 1.0 and about 9.4 kb from the left-hand EcoRI site (cf. FIG. 1) was necessary to code for Pap pilus formation and digalactoside-specific binding. Insertional mutants between 7.9 and 9.2 kb from the EcoRI site (cf. FIG. 1) abolished digalactoside-specific binding without inhibiting the formation of Pap pili.

EXAMPLE 3

Genetic characterization of pilus adhesin DNA

The region identified in Example 2 as necessary for Pap pilus formation and digalactoside-specific binding was recloned as a 9.6 kb long EcoRI-BamHI fragment of pRHU30 into pBR322 giving plasmids pPAP5 (see FIG. 2) and pPAP22, as described in Materials and Methods. Both pPAP5 and pPAP22 carry the entire EcoRI-BamHI insert, although pPAP22, due to a deletion in vector DNA, has a unique PvuII site in the papA structural gene. Plasmid pPAP23 with a frameshift mutation, papA1, was constructed by introducing an 8 bp long XhoI linker in the unique PvuII site in pPAP22 (cf. FIG. 3). In E. coli strain HB101, this frameshift mutant, unlike the wild-type, was not agglutinated by antiserum raised against purified Pap pili.

E. coli strain HB101 harbouring pPAP23 agglutinates human $P_1$-erythrocytes as well as digalactoside-coated latex beads. Hence, pPAP23/HB101 appears to express the same receptor binding specificity as HB101 carrying the wild-type pap operon on pPAP22 or pPAP5. Thus, inactivation of the pilin gene papA did not diminish the degree of digalactoside-specific agglutination in the assay employed.

Tn5 insertions in the distal part of pap DNA abolish hemagglutination but allow Pap pili to be formed. It was thus assumed that the genes mediating agglutination would be located in this region. To further investigate the importance of the polypeptides encoded here, the $SmaI_1$-BamHI fragment, shown in FIG. 2, was subcloned into pBR322 (see Materials and Methods). Since the resulting plasmid did not complement Tn5 insertions in the $SmaI_1$-BamHI region, the cloned fragment was put under the transcriptional control of the lacUV5 promoter (in order to ensure adequate transcription of the genes on the fragment) which was inserted into the plasmid as an EcoRI fragment derived from pSKS106 (see Materials and Methods). This construct, pPAP16 (cf. FIG. 2), complemented the four non-hemagglutinating Tn5 mutants with insertion points in the $SmaI_1$-BamHI fragment. The localisation of these mutants is shown in FIG. 3.

Figure 3:
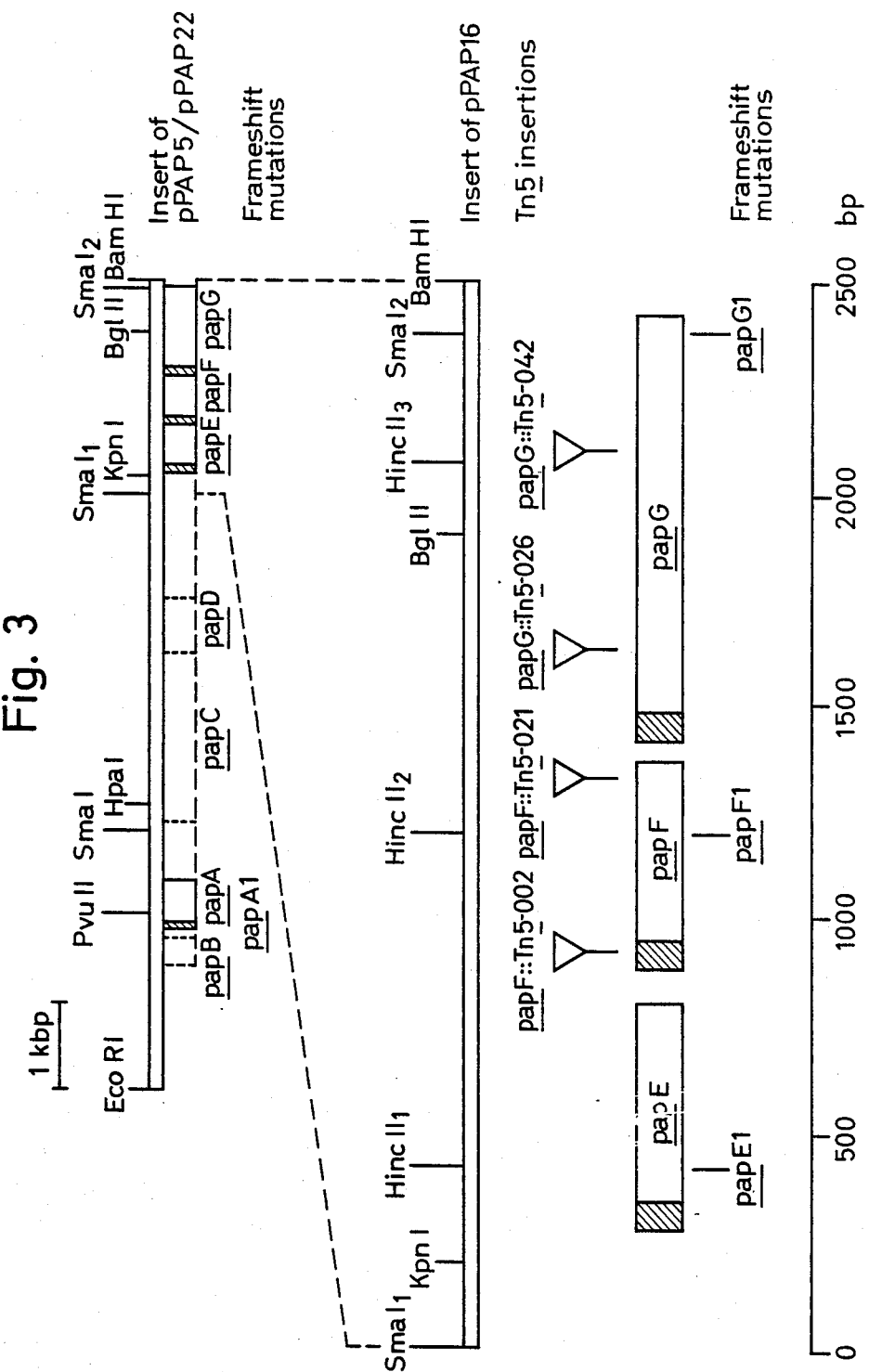
FIG. 3 shows the whole pap region as found in pPAP5 or pPAP22 (top half). pPAP22 is identical to pPAP5 except that it lacks the BamHI-PvuII part of the vector DNA. This plasmid is the parent of the papA1 derivative pPAP23. Also the position of the papA1 mutation is shown. The lower part of the figure shows the physical map of the SmaI$_1$-BamHI region. The positions of the Tn5 insertions in this region are shown. All destroy the capacity to mediate hemagglutination. Below this, the positions of the papE, papF and papG genes are shown. The hatched area represents the putative signal peptides which are believed to be encoded by those genes. Also the positions of the papE1, papF1 and papG1 mutations are shown. They have been introduced separately into both pPAP5 and pPAP16.

To further define the genes on the $SmaI_1$-BamHI fragment, a detailed restriction map of the pPAP16 insert was constructed with an accurate localisation of relevant Tn5 insertions (cf. FIG. 3). Three frameshift mutational derivatives of pPAP5 containing lesions in this region (cf. FIG. 3 and Materials and Methods) were also constructed. Two mutant plasmids, pPAP14 and pPAP15, carry XhoI linkers in the $HincII_2$ and $HincII_1$ sites, respectively. In a third mutant, pPAP7, pap DNA from $SmaI_2$ to BamHI (cf. FIG. 3) had been deleted.

The polypeptides expressed from pPAP5 and its three mutant derivatives were [$^{35}$S]methionine labelled in E. coli minicells, and the polypeptides expressed were analysed on a SDS-polyacrylamide gel. When compared with pPAP5, plasmid pPAP7 did not express the 35 kd polypeptide. Instead, a new polypeptide of 34 kd appeared. Since the mutation in pPAP7 truncated the pap region at the $SmaI_2$ site this would map the 3' end of the gene coding for the 35 kd polypeptide, papG, between the $SmaI_2$ and the BamHI sites (cf. FIG. 3). This is the last gene in the pap region.

The $HincII_2$ mutation in pPAP14 abolished expression of the 15 kd polypeptide, as do Tn5 insertions 002 and 021, which accurately maps the gene papF as encoding this polypeptide (cf. FIG. 3). No other polypeptides were affected by the $HincII_2$ mutation (papF) in pPAP14. The minicell preparation of the $HincII_1$ linker insertion mutant, pPAP15, does not produce the 16.5 kd polypeptide. The gene for this polypeptide is termed papE and the frameshift mutation is referred to as papE1. The truncation of the papG gene products by the $SmaI_2$-BamHI deletion shows that this gene is transcribed from left to right in FIG. 3. Polarity effects exerted by Tn5 insertions in papE and papF on papG show that the transcription of all three genes is in this direction.

To confirm the position of the Tn5 mutations relative to the papF and papG genes, the Tn5 mutations 002, 021, 026 and 042 (cf. FIG. 3) were complemented with the mutated $SmaI_1$-BamHI region. For this purpose, papE1, papF1 and papG1 derivatives of pPAP16 carrying the $SmaI_1$-BamHI region under lacUV5 promoter control were constructed as described in Materials and Methods. These were then transformed to E. coli strain HB101 carrying the Tn5 derivatives of pRHU845 (Normark et al., op. cit.) and assayed for globoside-specific hemagglutination using $P_1$- and p-erythrocytes. The papE1 derivative complemented all Tn5 mutations as did the parent plasmid pPAP16. The papF1 plasmid complemented Tn5 mutations 026 and 042, while the plasmid carrying papG1 complemented mutations 002 and 021. This defines the 002 and 021 Tn5 insertions as mutations in papF and shows that Tn5 insertions 026 and 042 reside in the papG gene. It also clearly shows that papF and papG are separate, independently trans-complementable genes. The genetic map of this region (shown in FIG. 3) was constructed on the basis of these data.

As indicated above, Tn5 insertions in papF and papG abolish hemagglutination completely, though pili are formed. To assess the individual importance for hemagglutination of the papE, papF and papG gene products, the non-polar linker insertion mutant derivatives of pPAPL5 in hemagglutination tests. It was found that neither the papF1 nor the papG1 derivative showed any agglutination of $P_1$-erythrocytes, demonstrating that both the papF and the papG gene products are needed for agglutination. The papE1 mutant did not by itself affect the hemagglutination titer, but surprisingly a papA1, papE1 double mutant, pPAP26, did not agglutinate $P_1$-erythrocytes when transformed to E. coli strain HB101.

The pilus antigen formation and digalactoside-specific binding properties of the various mutant derivatives of pPAP5 or pPAP22 in E. coli strain HB101 are summarized in Table 1.

TABLE I

Characterstics of plasmids used for mapping and functional analyses of papA, papE, papF and papG

| Plasmid | Relevant genotype | Phenotype Pilus-antigen | Hemmagglu-tination |
|---|---|---|---|
| pSN002 | papF::Tn5-002 | + | − |
| pSN021 | papF::Tn5-021 | + | − |
| pSN026 | papG::Tn5-026 | + | − |
| pSN042 | papG::Tn5-042 | + | − |
| pPAP5 | wild-type | + | + |
| pPAP15 | papE1 | + | + |
| pPAP14 | papF1 | + | − |
| pPAP7 | papG1 | + | − |
| pPAP20 | papE1, ΔpapF-G | + | − |
| pPAP19 | papF1, ΔpapG | + | − |
| pPAP22 | wild-type | + | + |
| pPAP23 | papA1 | − | + |
| pPAP26 | papA1, papE1 | − | − |
| pPAP9 | ΔpapB-D | − | − |
| pPAP1 | ΔpapB-D, papG1 | − | − |
| pPAP16 | ΔpapB-D, lacP$_{UV5}$ | − | − |
| pPAP18 | ΔpapB-D, lacP$_{UV5}$, papE1 | − | − |
| pPAP17 | ΔpapB-D, lacP$_{UV5}$, papF1 | − | − |
| pPAP4 | ΔpapB-D, lacP$_{UV5}$, papG1 | − | − | pSN plasmids are pACYC184 derivatives (carrying the EcoRI fragment from pRHU845; each plasmid contains a different Tn5 insertion as shown in FIG. 1), whereas pPAP plasmids are derivatives of pBR322. Pilus antigen was determined by slide agglutination of a cell suspension with antisera raised against Pap pili.

It appears from the table that mutation papA1 in pPAP23 completely abolished the formation of the major Pap pilus subunit (the papA gene product) without affecting digalactoside-specific binding. Conversely, mutation papF1 in pPAP14 and papG1 in pPAP7 abolished digalactoside-specific binding without inhibiting the formation of Pap pili.

Mutations in genes papC and papD abolished both pilus formation and digalactoside-specific binding. Only mutations in papF and papG lead to the abolition of the digalactoside-specific binding without preventing the formation of Pap pili. The only exception is the double mutant papA1-papE1 which is negative for agglutination as described above. Mutations in papA or papE only are adherent. This effect is assumed to be ascribable to the fact that the papA or papE polypeptides are (presumably) required to anchor the adhesin to the cell wall. It may therefore be concluded that the papF and/or papG genes encode the digalactoside-specific adhesion.

EXAMPLE 4

Establishing the DNA sequence of the pilus adhesin DNA

100 μg of pPAP9 (constructed as described in Materials and Methods; shown in FIG. 2) was digested with EcoRI and BamHI and subjected to preparative agarose gel electrophoresis in order to isolate the EcoRI-BamHI fragment containing the $SmaI_1$-BamHI region (cf. FIG. 3).

Aliquots of this fragment were digested with the enconucleases HaeIII, AsaI, AluI, HpaII, Sau3A, TaqI, HincII and BglII separately or in combination. Fragments obtained were either cloned directly or after preparative agarose gel electrophoresis, and fragment isolation performed into phage M13 vectors (M13 mp8 and M13 mp9; Messing et al., *Nucleic Acids Res.* 8, 1981, pp. 309–321). The inserts were sequenced using the method of Sanger et al., *Proc. Natl. Acad. Sci. USA* 74, 1977, pp. 5463–5467 (dideoxy sequencing) until unambiguous overlapping readings of the DNA sequence of the $SmaI_1$-BamHI fragment were obtained for both strands.

EXAMPLE 5

Amino acid sequencing of the pilus adhesins

Among the possible reading frames, the genes papE, papF and papG were identified from the known position of the genes established by means of linker and transposon Tn5 insertions (cf. FIG. 3) and the known size of their respective gene products, 16.5 kd, 15 kd and 35 kd, respectively. The N-terminal ends of these genes were identified. The amino acid sequence was derived from the DNA sequence using the genetic code established for *E. coli*. Since all the gene products are made as precursors containing single peptides, the 5'-end of the gene was assumed to be a methionine followed by a signal peptide-like sequence (G. von Heijne, *European Journal of Biochemistry* 133, 1983, pp. 17–21).

EXAMPLE 6

Homology with other uropathogenic *E. coli* DNA

Several fragments from the $SmaI_1$-BamHI region were isolated and $^{32}P$-labelled by nick translation. The fragments were selected so as to cover the entire region in small segments. These were then used as probes in Southern blots of digests of plasmids pDC5 (Clegg and Pierce, *Infect. Immun.* 42, 1983, pp. 900–906) and pPIL110-35 (van Die et al., *FEMS Microbiol. Letters* 19, 1983, pp. 77–82) under stringent conditions. Strong hybridization signals were obtained with probes from the papE and papF genes whereas no signals were obtained from the papG gene region. Strong hybridization under stringent conditions were also obtained from a probe of the papC gene between the HpaI sites at about 3.2–3.4 kb from the EcoRI site (cf. FIG. 1).

Detailed restriction maps of pDC5 and pPIL110-35 were constructed and found to be nearly identical with the restriction map of pPAP5 with respect to the papC and papD regions. A lesser, though still high degree of similarity was observed for the papE and papF genes. It may therefore be concluded that the DNA which encodes MRHA+ in other uropathogenic strains of *E. coli* is very similar to that cloned in pPAP5 (derived from *E. coli* strain J96) and that results obtained in the Pap system can be generalized to most pyelonephritogenic strains. As regards pPIL110-35, it has also been demonstrated that the MRHA expressed from its DNA is digalactoside-specific. Similar results were obtained with chromosomal DNA from clinical isolates by the present inventors as well as by other researchers (cf. Low et al., *Infect. Immun.* 43, 1984, pp. 353–358).

EXAMPLE 7

Construction of a fusion between the papG gene and the lacZ gene

Plasmid pPAP9 was digested with BglII and SalI (located about 375 bp to the right of the BamHI site in pPAP9). The resulting fragment was ligated to plasmid pMC874 (Casabadan et al., *J. Bacteriol.* 143, 1980, pp. 971–980) which had previously been digested with BamHI and SalI. After transformation to pMC1061 (Casabadan et al., op. cit.) and plating on plates containing 100 μg/ml of ampicillin, recombinants were analyzed. A plasmid, pHMG51, consisting of pPAP9 in which the BGlII-SalI fragment had been replaced by the lac-casette from pMC874 (the BamHI-SalI fragment) was isolated and shown by minicell analysis as described in Materials and Methods to code for a papG-lacZ fusion peptide. This result was also expected from the known sequence of the papG gene and that of the lacZ gene as present in pMC874.

INSTRUCTIONS

A. Preparation of other fused genes

In an alternative method to that disclosed in Example 7, N-terminal DNA fragments comprising the papF gene are obtained by linearizing pPAP9 with BglII. This DNA is then incubated for increasing periods of time with the exonuclease ExoIII and then treated with nuclease S1 resulting in increasing deletions from the BglII site. HindIII linkers are attached. This DNA is then redigested with SmaI and HindIII and subjected to preparative agarose gel electrophoresis. Fragments ranging from 1,400 to 1,000 bp (cf. FIG. 3) are isolated and ligated into the appropriate fusion vector which has previously been digested with SmaI and HindIII as described below.

Fragments containing the papG gene are constructed by the method described above, but by digesting with BamHI instead of BglII. Fragments ranging from 2,400 to 1,500 bp on the gel (cf. FIG. 3) are selected. Fragments containing the papE gene are constructed in the same manner, selecting fragments ranging from 800–400 bp (cf. FIG. 3).

DNA fragments encoding the N-terminal portion of the papF gene are cloned into a fusion vector such as pSKS104, pSKS105 or pSKS106 (Casadaban et al., *Methods in Enzymology* 100, 1983, pp. 293–308) so as to create gene fusions with the lacZ gene. The fused gene in these constructions is transcribed by the lacUV5 promoter.

This construction is transformed to a strain containing the LacI$^q$ gene, e.g. E. coli strain JM103 (Messing et al., Nucleic Acids Res. 9, 1981, pp. 309–321), selecting for ampicillin resistance. This strain is then grown in a suitable medium such LB-broth (G. Bertani, J. Bacteriol. 62, 1951, pp. 293–300) to an optical density of OD 600=0.4. Transcription of the fused gene is then induced by adding IPTG (J. Miller, Experiments in Molecular Genetics, Cold Spring Harbor, N.Y., 1972). Incubation is continued until maximum expression of the fused gene product has been obtained. The cells are then harvested and the fused gene product is purified by standard methods using an assay for β-galactosidase activity (cf. J. Miller, op. cit.). The purified fusion product may then be used directly in vaccine tests in e.g. rodents, monkeys or swine.

B. Preparation of a vaccine

The entire papE, papF or papG gene products or appropriate fragments thereof for use as vaccine are prepared in either of the following ways:

1. The purified fusion proteins of the lacZ gene and papE, papF or papG genes are digested with a suitable protease, e.g. trypsin or chymotrypsin, or a chemical reagent such as cyanogen bromide or hydroxyl amine. The desired peptide is obtained from the resulting peptide mixture by standard techniques, e.g. ion exchange chromatography or HPLC reverse phase chromatography.

2. Alternatively, antibodies against the fusion proteins are raised by injecting these into rabbits. The resulting antibodies can be used for the purification of the non-fused, pure papE, papF or papG gene products from a lacZ$^-$ bacterium containing a plasmid carrying these genes. This plasmid may be a pBR322 derivative such as pPAP5 or pPAP16, or a runaway plasmid derivative such as pBEU28 (Uhlin et al., Gene 22, 1983, pp. 255–265).

The purification is performed either by immunoaffinity gel chromatography or the antibody is used to develop an ELISA assay which is used to detect the polypeptides when developing a purification protocol (cf. Materals and Methods).

Fragments of these purified polypeptides may, if desired, be obtained by cleavage with protease etc. as described under 1.

3. Fragments consisting of 5–30 amino acids or more of the papE, papF and papG gene products are synthesized by solid phase peptide synthesis (Stewart and Young, Solid Phase Peptide Synthesis, Freeman & Co., San Francisco, USA, 1969). They may then be used for vaccination as much or coupled to a carrier molecule of a physiologically acceptable carrier such as poly-L-lysine or poly-D,L-alanine with or without an adjuvant substantially as described in Arnon, J. Immunological Methods 61, 1983, pp. 261–273.

C. The Pseudomonas system

Assuming that pilus formation and adhesion are linked in Pseudomonas species, chromosomal DNA from an adhering strain of Pseudomonas is digested with a restriction endonuclease to produce fragments which are cloned into a pBR322 derivative, a Pseudomonas/E. coli shuttle vector, a plasmid vector or a phage vector and transformed/transfected into E. coli. The bacteria harbouring the hybrid vector are screened for production of the major Pseudomonas pili subunit using antibodies raised against the purified Pseudomonas pili. (This has been done for N. gonorrhea using pBR322 as a vector; cf. Meyer et al., Cell 30, 1982, pp. 45–52).

This clone is then used directly or as a probe to obtain a larger DNA fragment containing the pilin gene. This fragment is then cloned into a Pseudomonas/E. coli shuttle vector which is transferred into a non-piliated, non-adhering strain of Pseudomonas which is then assayed for adhesion and pilus formation. Mutagenesis of this fragment is then performed in essentially the same way as described in Example 2 with respect to uropathogenic E. coli with the exception that the phenotypic assays are carried out in Pseudomonas instead.

Alternatively, if the chromosomal DNA is cloned directly into a Pseudomonas vector or a Pseudomonas/E. coli shuttle vector and transformed to a non-adhering strain of Pseudomonas, the clones can be screened for adhesion directly. Other assays may be used, for instance binding of the soluble receptor.

Fusion proteins and protein production in E. coli is performed in similar ways to those described above, though possibly transcription and translation initiation signals must be altered synthetically. Alternatively, protein production may be performed in a homologous system in Pseudomonas using e.g. the broad host range Tac promoter vectors described by Bagdasarian et al., Gene 26, 1983, pp. 273–282. DNA sequencing and amino acid analysis is carried out essentially as described in Examples 4 and 5 above, and on the basis of the sequence analysis, synthetic peptides may be produced as described above.

Similar methods as those described in Examples 1–5 as well as those outlined for Pseudomonas may be used to identify and produce putative adhesin polypeptides from other adhering bacteria such as Neisseria species, etc.

In principle, all investigations may be carried out using protein chemistry. The adhesin polypeptides may be enriched/purified by receptor, e.g. digalactoside, affinity chromatography or any other appropriate method (such as antibody affinity chromatography). The purity of the protein may be assayed by SDS-polyacrylamide gel electrophoresis as described in Materials and Methods. To ensure that the adhesins constitute a large fraction of the preparation, equilibrium dialysis experiments with the radioactively labelled receptor may be employed to calculate the number of binding sites per molecule of protein present. This is expected to be between 0.1 and 10 ligands per molecule of protein.

EXAMPLE 8

Materials and Methods Used in this Example

Bacterial strains, plasmids and growth conditions

All bacterial strains are E. coli K12 derivatives, except the clinical isolates described in Table 2. For protein expression analyses a recA derivative of P678-54 (1), AA10 was used. M13 cloning and phage propagation was carried out in JM103. HB101 was the host in all other experiments.

Plasmid pPAP5 (cf. General Materials and Methods above) is a pBR322 derivative carrying a 9.5 kb EcoRI-BamHI chromosomal fragment isolated from E. coli J96. This clone expresses an F"CI34.3" pilus antigen which is serologically related to FI2. The gene map of the pap cluster is shown in FIG. 1. Plasmid pDC5 is a pACYC184 derivative carrying an 8.0 kb ClaI-BamHI fragment of E. coli IA2, whereas pPIL110-35 is a pACYC184 derivative containing a 16 kb EcoRI fragment isolated from E. coli AD110 responsible for the formation of F7$_2$ pilus antigen.

The following concentrations of antibiotics were used for selection: carbenicillin 100 μg/ml, tetracycline 15 μg/ml, kanamycin 20 μg/ml and chloramphenicol 20 μg/ml. Bacteria were grown at 37° C. in Luria broth or on Luria agar.

General procedures

The CaCl$_2$ procedure was used for transformation. Plasmid DNA was isolated by a modification of the alkaline clear lysate procedure of Birnboim H. C. and J. Doly ("A rapid alkaline extraction procedure for screening recombinant plasmid DNA" *Nuclear Acids Res.* 7, 1979, pp. 1513-1523) and Grosveld at al. ("Isolation of β-globin-related genes from a human cosmid library", *Gene* 13, 1981, pp. 227-237) followed by two consecutive ethidium bromide/CsCl equilibrium centrifugations. Restriction endonucleases were used under the conditions recommended by the manufacturers (New England BioLabs, USA, Boehringer Mannheim GmbH or Bethesda Research Laboratories GmgH). Digested DNA was separated on 0.5% to 1.5% (wt/vol) agarose gels. Phage λ DNA and phage φX174 DNA cleaved with HindIII and HaeIII, respectively (New England Biolabs) were used as molecular weight standards. DNA fragments were obtained in pure form by electroelution from 5% (wt/vol) polyacrylamide gels.

Blotting and hybridization procedures

[$^{32}$P]-labelled DNA probes were prepared by nick-translation or by priming DNA synthesis of cloned M13 single stranded DNA templates with an M13 hybridization probe primer (New England BioLabs). [α$^{32}$P]dGTP (Amersham, England) was incorporated to a specific activity of approximately 1×10$^8$ cpm/μg. Plasmid DNA, size fractionated on agarose gels, was transferred to nitrocellulose filters (Schleicher and Schüll, BA85) according to Southern, E. M., "Detection of specific sequences among DNA fragments separated by gel electrophoresis", *J. Mol. Biol.* 98, 1975, pp. 503-517. The blotted filters were prehybridized for 2 hours at 68° C. in a hybridization solution consisting of: 4×SSC (1×SSC is 150 mM NaCl; 15 mM Na citrate pH 7.0), 10× Denhardt's solution, 0.1% SDS, 2 mM EDTA and sonicated calf thymus DNA at 50 μg/ml. Radiolabelled probe in fresh hybridization solution (1×10$^6$ cpm/ml) was then added to the filters which were incubated for 18 hours in plastic bags. For stringent conditions, hybridization was performed at 68° C., and washes were conducted at the same temperature in salt concentrations from 2×SSC; 0.1% SDS down to 0.1×SSC; 0.1% SDS. Non-stringent hybridization was carried out under similar conditions, except that the hybridization temperature was 55° C. and that washes were done in 2×SSC. Filters were exposed overnight to Dupont Cronex 4 X-ray film with an intensifying screen.

Analyses of protein expression in minicells

Plasmids pPAP5, pPAP502, pDC5 and pPIL10-35 were transformed into the minicell producing strain AA10. Preparation and labelling of minicells with [$^{35}$S]-methionine (Amersham) was as described by Thompson, R., and M. Achtman, "The control region of the F sex factor DNA transfer cistrons: restriction mapping and DNA cloning", *Mol. Gen. Genet.* 165, 1978, pp. 295-304. The radioactive samples were separated on linear 15% (wt/vol) SDS-polyacrylamide gels. The gels were subsequently fixed, stained, destained, enhanced (Enhance, New England Nuclear GmbH) and exposed to X-ray film for 1-6 days. Molecular weight standards were from Pharmacia Fine Chemicals, Sweden.

Nucleotide sequence determination

Relevant fragments were cloned into phase M13 cloning vectors M13mp8 and M13mp9 and transformed into *C. coli* strain JM103. Single stranded template DNA was isolated from the phage as described by Messing et al. "A system for shotgun DNA sequencing", *Nucleic Acids Res.* 9, 1981, pp. 309-321. The DNA sequences were determined by the dideoxy chain termination method of Sanger et al., "DNA sequencing with chain-terminating inhibitors", *Proc. Natl. Acad. Sci. USA* 74, 1977, pp. 5463-5467, utilizing the M13 pentadecamer sequencing primer (New England Biolabs).

Receptor binding assays

The binding properties of the gene products encoded by the plasmids listed in Tables 1 and 2 were determined by slide agglutination as described in General Materials and Methods above using P$_1$-erythrocytes containing the globoside receptor and p-erythrocytes which lack the globoside.

Pilus antigen assay

Slide agglutination, utilizing antisera raised against purified Pap pili (37) were performed as described in General Materials and Methods above. Antiserum was used as a 500-fold dilution in PBS (pH 7.5).

Construction of plasmid derivatives for complementation analyses

Plasmid pPAP43 is a derivative of pPAP5, obtained by SmaI digestion followed by ligation at low DNA concentration. This plasmid lacks the SmaI$_1$-SmaI$_4$ region of pPAP5 (FIG. 1) and consequently carries only the genes papB and papA. In order to construct the cutback derivative pPAP502, plasmid pDC5 (FIG. 1) was completely digested with BglII, and partially digested with BamHI, followed by religation and transformation into HB101. Plasmid DNA was isolated from the transformants and screened for the calculated size. One clone, pPAP502, with the correct size was further analyzed and as expected, the papG gene was absent (cf. Table 3). Plasmid pPAP503 was constructed by ligating an EcoRI-HindIII fragment from pSKS106 carrying the lac promoter and the rightmost HindIII-BamHI fragment of pDC5 to pBR322 digested with EcoRI and BamHI. Plasmid pPAP504 was obtained by digesting pPAP503 with BglII and BamHI, followed by religation at low DNA concentration. The plasmid pPAP507 was constructed by cloning the HindIII fragment of pDC5 carrying the genes equivalent to papA, papH and papC into the unique HindIII site of pPAP503 selecting for ampicillin resistance and screening for hemagglutination. Ths intermediate (pPAP506) was subsequently digested with BglII and BamHI followed by religation giving pPAP507 in a manner analogous to the construction of pPAP504 from pPAP503.

Electron microscopy

Electron microscopy was performed using a JEOL 100B microscope with 100 mesh copper grids coated with thin films of 2% formvar. Bacteriz were resuspended in 10 mM Tris HCl (pH 7.5); 10 mM MgCl$_2$ and placed on the grid. The excess was immediately removed by aid of a filter paper. Grids were then washed with buffer and negatively stained for 5 seconds with 3.55% ammonium molybdate followed by washing with redistilled water.

Results

Structural comparison of pPAP5 to pDC5 and pPIL10-35

All three plasmids were shown to encode globoside-binding specificity (Table 2) The chromosomal inserts of the plasmids were mapped with several restriction endonucleases. To allow the detection of even small discrepancies in fragment size, the restriction enzyme digests of the different plasmids were analyzed in parallel slots by agarose gel electrophoresis. As shown in FIG. 1, the central $SmaI_1$-KpnI fragment is of the same size (4.6 kb) in all three plasmids. In pPAP5 this fragment codes for part of an additional gene as well as for the papC and papD genes. No differences were found in the physical map of this central fragment. Furthermore, a PstI fragment, approximately 370 bp in size and derived from the coding region of papC in pPAP5, hybridizes to a PstI fragment of equal size in pDC5 and pPIL110-35. Likewise, a 128 bp HpaI fragment from the N-terminal region of papC hybridizes to identically sized HpaI fragments from pDC5 and pPIL110-35. These observations show that the central region of the globoside-binding gene clusters, believed to encode export and assembly functions, is highly conserved.

Plasmid pPIL110-35 carries a 5.7 kb DNA fragment that extends leftwards of the conserved $SmaI_1$-KpnI region. This region encompasses the structural gene for the $F7_2$ pilin, which holds a position equivalent to papA. The restriction site homology is not conserved in this region (FIG. 1). Also, a 221 nucleotide long probe from the central region of papA gave only a weak hybridization signal with pPIL110-35 even at low stringency, although the very 5' region of papA hybridized strongly under stringent conditions. This implies that the 5' end of the two pilin genes is highly conserved, whereas the central region appears to have diverged markedly.

A DNA probe derived conventionally from the coding part of papB gave a strong hybridization signal with the 6.0 kb HindIII fragment of pPIL110-35, suggesting that this gene is conserved and is present in equivalent positions in the two clones.

Three genes, papE, papF and papG, have been mapped to the $SMaI_3$-BamHI fragment of pPAP5. The restriction pattern of this fragment is less conserved in pDC5 and pPIL110-35 than is the central $SmaI_1$-KpnI fragment. The $SmaI_3$-BglII fragment of pPAP5 carries papE, papF and the 5' half of papG. Using this fragment as a probe in Southern blotting experiments, signals of equal strength were detected in all three plasmids analyzed. The fragments that hybridize hold equivalent positions in the physical map of the three plasmids. On the other hand, a BglII-$SmaI_4$ probe carrying the 3' half of papG, while giving a strong signal with pPAP5 DNA, did not hybridize to pDC5 or pPIL110-35 DNA even at low stringency. It should be noted that these two plasmids encode proteins that have a size similar to that of papG from this region. They also appear to have a similar restriction pattern, different from pPAP5, in the papG region. To more precisely define the borderline between homology and non-homology, a large number of M13 clones carrying defined regions of papE, papF and papG were used. Nick translated pDC5 and pPIL110-35 were used as probes. Positive hybridizations were detected with all M13 probes containing papE and papF DNA. None of the M13 clones carrying only papG DNA gave a positive signal. Thus, papE and papF are conserved, whereas there is a sharp decline in homology close to the end of papF and the start of papG.

Protein expression in minicells

Proteins expressed from pPAP5, pDC5 and pPIL110-35 were [$^{35}$S]-methionine labelled in *E. coli* minicells and the radiolabelled gene products were analyzed on 15% SDS-polyacrylamide gels. Proteins of similar molecular weight as papB and papA of pPAP5 were expressed from pPIL110-35, but not from pDC5. Both pDC5 and pPIL110-35 have been shown to express a protein, 71-75K (Clegg, S., and J. K. Pierce, "Organization of genes responsible for the production of mannose-resistant fimbriae of a uropathogeneic *Escherichia coli* isolate", *Infect. Immun.*, 42, 1983, pp. 900-906, and van Die, I. et al., "Molecular organisation of the genes involved in the production of $F7_2$fimbriae, causing mannose resistant haemagglutination, of a uropathogenic *Escherichia coli* 06:K2:H1:F7 strain, *Mol. Gen. Genet.* 194, 1984, pp. 528-533), mapping approximately at the same position as papC of pPAP5. The papC gene products of pDC5 and pPIL110-35 appeared as weakly expressed proteins with a slightly lower molecular weight than the PapC protein of pPAP5, whereas both pDC5 and pPIL110-35 expressed a protein with the same molecular weight as the PapD protein. For pPIL110-35 the gene encoding this protein has been mapped to the region corresponding to papD (van Die, I. et al., "Molecular organisation of the genes involved in the production of $F7_2$fimbriae, causing mannose resistant haemagglutination, of a uropathogenic *Escherichia coli* 06:K2:H1:F7 strain, *Mol. Gen. Genet.* 194, 1984, pp. 528-533). The PapE protein of pPAP5 has an apparent molecular weight of 16.5K. It was not possible to detect a protein of the same size in pDC5 and pPIL110-35, however, the slightly smaller protein expressed from both plasmids could be the papE gene product of these gene clusters. All three plasmids expressed a 15K protein which is known to be encoded by papF that is essential for globoside binding. The PapG protein of pPAP5 is a 35K polypeptide; and in both pDC5 and pPIL110-35 proteins with a slightly higher molecular weight were found. The BglII-BamHI cutback derivative of pDC5, pPAP502, did not express the 36K polypeptide. This localizes the gene for this protein to the same region as papG in pPAP5.

A highly expressed 17K polypeptide from pDC5 and pPIL110-35 has been assigned to the distal SmaI-BamHI fragment of these plasmids (Clegg, S., and J. K. Pierce, "Organization of genes responsible for the production of mannoseresistant fimbriae of a uropathogeneic *Escherichia coli* isolate", *Infect. Immunol.* 42, 1983, pp. 900-906, and van Die, I. et al., "Molecular organisation of the genes involved in the production of $F7_2$fimbriae, causing mannose resistant haemagglutination, of a uropathogenic *Escherichia coli* 06:K2:H1:F7 strain, *Mol. Gen. Genet.*, 194, 1984, pp. 528-533). The pPAP5 constructs lack DNA equivalent to this region, consequently the 17K protein is not expressed from these plasmids or from pPAP502.

Complementation between the gene clusters on pPAP5 and pDC5

Since pDC5 contains DNA highly homologous to papC, papD, papE and papF, the question arose if pDC5 could be complemented by papA in pPAP5 to bring about the formation of a papA pilus. Consequently, pPAP43, which carries only the papB and papA genes and cannot surface localize the papA antigen, was constructed. Neither HB101 carrying this plasmid, nor the same strain with pDC5 was agglutinated by anti-pilus antiserum. When both these compatible plasmids were present in the same cell, however, the papA pilin was surface localized as demonstrated by antiserum agglutination. By electron microscopy it was confirmed that the papA pilin was assembled in the form of pili (data not shown). Neither pPAP43 nor pDC5 alone expressed surface localized pili when harbored in HB101.

To see if the adhesion function also could be complemented between the gene clusters, pPAP502 lacking the DNA from the BglII site to the BamHI site at the rightmost end of pDC5 was constructed. Compared to pDC5, this derivative failed to express a 36K and a 17K polypeptide in minicells. It is assumed that, in agreement with mapping and hybridization data, the 36K protein corresponds to the 35K protein encoded by papG of thr pap gene cluster. Plasmid pPAP502, in contrast to pDC5, did not mediate hemagglutination. Using pPAP16, a plasmid expressing papE, papF and papG in pPAP5, in trans it was possible to complement the deletion derivative pPAP502 to hemagglutination. Thus, also the adhesin function can be trans-complemented from one gene cluster to another, which is surprising, since the papG region is not well conserved between the clones. Plasmids pPAP18, pPAP17 and pPAP4 which are papE1, papF1 and papG1 mutants of pPAP16, (cf. General Materials and Methods above), respectively, failed to complement the deletion on pPAP502. Plasmid pPAP503, containing the HindIII-BamHI fragment of pDC5 under lac promoter control also failed to hemagglutinate. However, pPAP503 could complement the defect in pPAP502 as shown by the positive hemagglutination reaction obtained with cells containing both these plasmids. As expected, a BglII-BamHI deletion derivative of pPAP503 failed to accomplish this complementation (pPAP504 in Table 3). These plasmids were used to complement mutations in the pap clone. It was shown that pPAP503 complemented all Tn5 insertion mutants in papF and PapG, whereas the cutback derivative pPAP504 only complements those in papF (Table 3). The pDC5 derivative pPAP507 encoding the papC, papD, papE and papF gene equivalents complemented pSN021 carrying a Tn5 mutation in th papF gene. These results show that proteins functionally similar to the papF and papG gene products are encoded by the corresponding regions on pDC5. From the experiments in the present Example, it may be concluded that the papA gene and to some extent the papG gene exhibit variability over the three E. coli strains, whereas the papF gene exhibits very little variability. It is not possible to decide whether papG or papF encodes for the specific binding protein.

TABLE 2

Characteristcs of E. coli UTI strains and plasmid clones encoding their respective adhesin

| Isolate | Serotype of isolate | Designation of plasmid clone | Serotype of cloned pilus antigen | Cloned specificity of binding |
|---------|---------------------|------------------------------|----------------------------------|-------------------------------|
| J96     | 04:K6:H5            | pPAP5                        | F. "CI34.3"                      | Globoside                     |
| IA2     | 06:H-               | pDC5                         | N.D.                             | Globoside                     |
| AD110   | 06:K2:H1            | pPIL110-35                   | F$7_2$                           | Globoside                     |

TABLE 3

Surface expression of globoside-specific adhesin by complementation between pap genes of pPAP5 and pDC5

| Plasmid  | Mutation           | —   | pSNO21 papF::Tn5-021 | pSNO42 papG::Tn5-042 | pPAP502 Δ[papG] |
|----------|--------------------|-----|----------------------|----------------------|-----------------|
| —        |                    | —   | —                    | —                    | —               |
| pPAP16   | wt                 | —   | +                    | +                    | +               |
| pPAP18   | papE1              | —   | +                    | +                    | —               |
| pPAP17   | papF1              | —   | —                    | +                    | —               |
| pPAP4    | papG1              | —   | +                    | —                    | —               |
| pPAP503  | Δ[papB-D]          | —   | +                    | +                    | +               |
| pPAP507  | Δ[papG]            | —   | +                    | —                    | —               |
| pPAP504  | Δ[papB-D], Δ[papG] | —   | +                    | —                    | —               |

EXAMPLE 9

Hybridization of clinical isolates of E. coli

Materials and Methods Used in this Example

Bacterial strains and plasmids

The specimens consisted of 66 isolates of E. coli, collected from the urine of patients with significant bacteriuria ($>10^5$ bacteria/ml) and 96 fecal E. coli isolates obtained from healthy individuals. Plasmid pPAP5 carries a Xxb large EcoRI-BamHI fragment from E. coli J96(0:4) that contains the entire paper gene cluster. The gene organisation is shown in FIG. 2. Plasmid pDC5 codes for the globoside specific adhesin of the uropathogenic E. coli strain IA2(0:6). Recently it was shown that these two plasmids shown extensive homology over the major part of the pap gene cluster. However, DNA of pPAP5 derived from the papG gene did not hybridize to pDC5. DNA sequencing has confirmed extensive differences between the papG genes in the two clones (Lund et al., to be published).

Media and growth conditions

The complete medium was Luria broth medium of Bertani supplemented with medium E and 0.2% glucose. The bacteria were grown at 37° C. with shaking. Luria broth agar plates without glucose were used for agglutination assay.

Receptor-binding assay

For identification of digalactoside binding E. coli, bacterial cells grown for 22 hours on glucose-free Luria broth agar were resuspended in a solution of latex beads coated with the digalactoside receptor. The cells were considered to express the adhesin if they agglutinated the beads within one minute.

Preparation of chromosomal DNA

Each bacterial isolate was grown in 100 ml LB-medium to $4\times10^8$ cells/ml. The bacteria were collected by centrifugation, suspended in 40 ml PBS (100 mM K-phosphate buffer, pH 7.2, 150 mM NaCl), recentrifugated and suspended in 5 ml PBS+0.1 mg/ml proteinase K, 5 mM EDTA and 0.5% SDS (sodium dodecyl sulphate). The suspensions were incubated overnight at room temperature and finally extracted with phenol and precipitated with ethanol, repeated twice.

Preparation of $^{32}$P-radiolabelled DNA fragments

Plasmids pPAP5 and pDC5 were digested with the appropriate restriction enzymes and DNA fragments were purified and $^{32}$P-labelled by nicked translation.

Blotting and hybridization procedures

A dot-blot procedure was followed. 2 μg of chromosomal DNA was dissolved in 170 μl 0.1M Tris (pH 7.4). After the addition of 30 μl 2M NaOH and 100 μl 3M NaCl-0.3M sodium citrate, the mixture was incubated at 80° C. for 20 minutes. The denatured DNA was chilled, neutralized with 40 μl 2M Tris (pH 7) and sucked through a 7 mm² area on a nitrocellulose filter, air dried and then baked in vacuo at 65° C. for 12 hours. The filters were incubated for 2 hours in 10×Denhardt (Denhardt=0.02% polyvinylpyrrolidone, 0.02% Ficoll, 0.02% BSA). They were once again incubated in a solution containing 4×SSC, 0.1% SDS, 2 mM EDTA, 10×Denhardt and 50 μg/ml calf thymus DNA (heated for 3 minutes at 95° C.) and incubated for one hour at 65° C. Finally they were incubated with a radiolabelled probe in the same solution as described above for 16 hours in 60° C. and then washed in 4×SSC 2×5 minutes and 2×SSC 2×20 minutes at 60° C. and then air-dried. The filters were exposed to Dupont Cronex 4 X-ray film together with an intensifying screen at −70° C. and then developed.

TABLE 4

Distribution of MR adhesins and hybridization to papE, papF and papG DNA

| Strain Nr. 1 Urinary tract isolates | | ADHESINS | | | | | | DNA hyb. probe | | |
|---|---|---|---|---|---|---|---|---|---|---|
| | | Human | | | | | | | Pap G | |
| | | PI | p | Swine | Sheep | Cow | Galgal | Pap E,F | J96 | Pap G |
| | J 96 | + | | + | | + | + | + | + | + |
| 3163u | 001 | + | + | | | + | + | + | | |
| 12007 | 002 | | | | | | | | | |
| 12014 | 003 | | | | | | | | | |
| 12061 | 004 | + | | + | + | | + | + | | + |
| 12081 | 005 | | | | + | | + | + | | + |
| 12088 | 006 | | | | | | | | | |
| 12118 | 007 | | | | | | | | | + |
| 12121 | 008 | | | | | | | | | |
| 12144 | 009 | + | + | | + | + | + | + | | + |
| 12154 | 010 | | | | | | | | | |
| 12159 | 011 | | | | + | | + | + | | + |
| 12257 | 012 | | | | | + | | | | |
| 12268 | 013 | | | | | + | + | + | | + |
| 12295 | 014 | + | + | | | + | | | | |
| 12297 | 015 | | | | | | | | | |
| 12335 | 016 | + | | + | | | + | + | | + |
| 12340 | 017 | + | | | | | + | + | | + |
| 12382 | 018 | | | | | | | | | |
| 12383 | 019 | + | | + | + | | + | + | | + |
| 12389 | 020 | + | | + | | | + | + | | + |
| 12390 | 021 | | | | | | | | | |
| 12392 | 022 | | | | | | | | | |
| 12409 | 023 | | | + | + | | + | + | | + |
| 12418 | 024 | + | + | | | | | | | |
| 12444 | 025 | | | | | | | | | |
| 12459 | 026 | | | | | | | | | |
| 12483 | 027 | + | | + | + | | + | + | | + |
| 12496 | 028 | + | | + | + | | + | + | | + |
| 12497 | 029 | | | | | | | | | |
| 12501 | 030 | + | | + | + | | + | + | | + |
| 12516 | 031 | + | | + | | + | + | + | | + |
| 12564 | 032 | | | | | | | | | |
| 12568 | 033 | | | | | | | | | |
| 12230 | 034 | + | | + | | | + | + | | + |
| 12571 | 035 | | | | | + | + | + | | + |
| 12620 | 036 | + | | + | | | + | + | | + |
| 12627 | 037 | | | | | | | | | |
| 12640 | 038 | | | | | | | | | |
| 12654 | 039 | | | | + | | | | | |
| 12672 | 041 | | | | | | | | | |
| 12708 | 042 | | | | | + | + | + | | + |
| 12724 | 043 | | | | | | | | | |
| 12725 | 044 | + | | + | | | + | + | | + |
| 12722 | 045 | + | | | | | | | | |
| 12727 | 046 | + | | + | | + | + | + | | + |
| 12755 | 047 | | | | | | | | | |
| 12756 | 048 | + | | | | | + | + | | + |
| 12767 | 049 | | | | | | | | | |
| 12782 | 050 | + | | | | | + | + | | + |
| 12908 | 051 | | | | | | | | | |
| 12933 | 052 | | | | | | | | | |
| 12970 | 053 | | | | | | | | | |
| 13047 | 054 | + | | | | | + | + | | + |
| 13058 | 055 | | | | | | | | | + |
| 13060 | 056 | | | | | | | | | + |
| 13122 | 057 | + | + | | | | | | | + |
| 13131 | 058 | + | + | | | | | + | | + |
| 13147 | 059 | | | | | | | | | |
| 13176 | 060 | | | | | | | | | |
| 13177 | 061 | | | | | | | | | |
| 13236 | 062 | | | + | + | | + | + | | |
| 13341 | 063 | + | + | | | | | | | + |

TABLE 4-continued
Distribution of MR adhesins and hybridization to papE, papF and papG DNA

| | | | | | | | | | |
|---|---|---|---|---|---|---|---|---|---|
| 13347 | 064 | | | | | | | | |
| 13388 | 065 | | | | | | | | |
| 13389 | 066 | | | | + | + | + | | + |
| 13781 | 067 | | | | | | | | |

| | Strain Nr. 1 Faecal tract isolates | ADHESINS | | | | | | DNA hyb. probe | | |
|---|---|---|---|---|---|---|---|---|---|---|
| | | Human | | Swine | Sheep | Cow | Galgal | Pap E,F | Pap G J96 | Pap G pDC5 |
| | | PI | p | | | | | | | |
| 2103 | 001F | + | | | | | + | + | | + |
| 2104 | 002F | | | | | | | | | |
| 2109 | 003F | | | | | | | | | |
| 2110 | 004F | | | | | | | | | |
| 2111 | 005F | + | + | | | | − | + | | + |
| 2112 | 006F | | | | | | | | | |
| 2113 | 007F | | | | | | | | | |
| 2124 | 008F | | | | | | | | | |
| 2130 | 009F | | | | | | | | | |
| 2133 | 010F | | | | + | | − | | | + |
| 2134 | 011F | | | | | | | | | + |
| 2138 | 012F | | | | | | | | | |
| 2139 | 013F | | | | | | | | | |
| 2140 | 014F | | | | | | | | | |
| 2145 | 015F | | | | | | | | | + |
| 2146 | 016F | + | + | | | | − | + | | |
| 2155 | 017F | | | | | | | | | |
| 2157 | 018F | | | | | | | | | |
| 2162 | 019F | | | | | | | | | + |
| 2171 | 020F | | | | | | | | | + |
| 2172 | 021F | | | | | | | | | |
| 2173 | 022F | + | | | | | + | + | | + |
| 2174 | 023F | + | + | | | | − | + | | + |
| 2177 | 024F | | | | | | | | | |
| 2179 | 025F | | | | | | | | | |
| 2182 | 026F | | | | | | | | | |
| 2186 | 027F | | | | | | | | | |
| 2187 | 028F | | | | | | | | | |
| 2188 | 029F | | | | | | | | | |
| 2189 | 030F | | | | | | | | | |
| 2190 | 031F | | | | | | | | | |
| 2191 | 032F | | | | | | | | | |
| 2195 | 033F | | | | | | | | | |
| 2196 | 034F | | | | | | | | | |
| 2197 | 035F | | | | | | | | | |
| 2198 | 036F | | | | | | | | | |
| 2200 | 037F | | | | | | | | | |
| 2201 | 038F | | | | | | | | | |
| 2204 | 039F | | | | | | | | | |
| 2205 | 040F | | | | | | | | | |
| 2212 | 041F | | | | | | | | | |
| 2213 | 042F | | | | | | | | | |
| 2214 | 043F | | | | | | | | | |
| 2216 | 044F | | | | | | | | | |
| 2218 | 045F | | | | | | | | | |
| 2219 | 046F | | | | | | | | | +/− |
| 2224 | 047F | | | | | | | | | |
| 2225 | 048F | + | | + | + | | + | + | | |
| 2226 | 049F | | | | | | | | | |
| 2227 | 050F | | | | | | | | | +/− |
| 2229 | 051F | | | | | | | | | +/− |
| | 052F | | | | | | | | | |
| | 053F | | | | | | | | | |
| | 054F | | | | | | | | | |
| 2234 | 055F | | | | | | + | + | | +/− |
| | 056F | | | | | | | | | |
| | 057F | | | | | | | | | |
| 2240 | 058F | + | + | | | | + | + | | +/− |
| | 059F | | | | | | | | | |
| | 060F | | | | | | | | | |
| | 061F | | | | | | | | | |
| | 062F | | | | | | | | | |
| | 063F | | | | | | | | | |
| | 064F | | | | | | | | | |
| | 065F | | | | | | | | | |
| 2249 | 066F | | | | | + | − | | | |
| | 067F | | | | | | | | | |
| | 068F | | | | | | | | | |
| | 069F | | | | | | | | | |

TABLE 4-continued

Distribution of MR adhesins and hybridization to papE, papF and papG DNA

| | | | | | | |
|---|---|---|---|---|---|---|
| | 070F | | | | | |
| | 071F | | | | | |
| | 072F | | | | | |
| | 073F | | | | | |
| | 074F | | | | | |
| | 075F | | | | | |
| | 076F | | | | | |
| 2265 | 077F | | − | | +/− | |
| | 078F | | | | | |
| | 079F | | | | | |
| | 080F | | | | | |
| | 081F | | | | | |
| | 082F | | | | | |
| | 083F | | | | | |
| | 084F | | | | | |
| | 085F | | | | | |
| | 086F | | | | | |
| | 087F | | | | | |
| 22286 | 088F | | | | +/− | |
| | 089F | | | | | |
| | 090F | | | | | |
| | 091F | | | | | |
| 22290 | 092F | + | + | − | + | |
| | 093F | | | | | |
| | 094F | | | | | |
| | 095F | | | | | |
| | 096F | | | | | |

Hybridization hemagglutination results on *E. coli* isolates used in this study

| | ISOLATES | |
|---|---|---|
| | Urine | Fecal |
| P-spec MRHA | 17 | 4 |
| p-spec MRHA | 7 | 3 |
| Z-spec MRHA | 10 | 3 |
| Total MRHA | 34 | 10 |
| Non MRHA | 32 | 86 |

| | Urine strains (66 st) | | | | Faecal strains (96 st) | | | |
|---|---|---|---|---|---|---|---|---|
| | Hybridization results | | | | | | | |
| | Pap E,F pPAP5 | | Pap G pDC5 | | Pap E,F pPAP5 | | Pap G pDC5 | |
| | pos | neg | pos | neg | pos | neg | pos | neg |
| P-spec MRHA | 16 | 1 | 16 | 1 | 4 | 0 | 3 | 1 |
| p-spec MRHA | 3 | 4 | 4 | 3 | 3 | 0 | 2 | 1 |
| Z-spec MRHA | 8 | 2 | 7 | 3 | 1 | 2 | 1 | 2 |
| Total MRHA | 27 | 7 | 27 | 7 | 8 | 2 | 6 | 4 |
| Non MRHA | 0 | 32 | 3 | 29 | 2 | 84 | 9 | 77 |
| Total number of strains | 27 | 39 | 30 | 36 | 10 | 86 | 15 | 81 |
| Latex beads positive | 26 | 0 | 24 | 2 | 5 | | | |
| Latex beads negative | 1 | 39 | 6 | 34 | 5 | | | |
| Total number of strains | 27 | 39 | 30 | 36 | 10 | | | |

P-spec MRHA: including strains that also agglutinate animal erythrocytes.
p-spec MRHA: erythrocytes that agglutinate human p-blood.
Z-spec MRHA: no hemagglutination to human erythrocyes but to any of the following animal erythrocytes: Swine, sheep, cow.

The results obtained in this Example demonstrate that a large number of the clinical isolates of *E. coli* strains that bind to digalactoside have the E, F and G regions in their pap operons, and that strains that do not bind digalactoside do not have the E, F and G regions of the pap operon although they have the other regions in the operon.

We claim:

1. An isolated antigen which comprises a pilus component distinct from pilin and substantially free from other components of the pilus, an immunogenically active subsequence of said component or a precursor for said component which is convertible to an immunologically active form, said antigen being one which elicits antibodies inhibiting the adhesion of pathogenic adhesin-forming bacteria to mammalian tissue.

2. An antigen according to claim 1 which comprises an amino acid sequence of at least 5 amino acids and up to the entire amino acid sequence of the pilus component.

3. An antigen according to claim 1 which binds to carbohydrate or protein receptors on mammalian tissue cells.

4. An antigen according to claim 3 which binds to a digalactoside-containing glycolipid or glycoprotein.

5. An antigen according to claim 1 which is derived from a pathogenic pilus-forming bacterium.

6. An antigen according to claim 5 in which the bacterium is a uropathogenic or enteropathogenic strain of

*Escherichia coli, Neisseria gonorrhoeae, Neisseria meningiditis; Neisseria catarrhalis, Pseudomonas spp., Moraxella spp.,* or *Bordetella spp.*

7. An antigen according to claim 6 in which the pathogenic strain of *E. coli* is a uropathogenic strain.

8. An antigen according to claim 1 which has the following amino acid sequence:

Met-Lys-Lys-Ile-Arg-Gly-Leu-Cys-Leu-Pro-Val-Met-Leu-Gly-Ala-Val-Leu-Met-Ser-Gln-His-Val-His-Ala-Val-Asp-Asn-Leu-Thr-Phe-Arg-Gly-Lys-Leu-Ile-Ile-Pro-Ala-Cys-Thr-Val-Ser-Asn-Thr-Thr-Val-Asp-Trp-Gln-Asp-Val-Glu-Ile-Gln-Thr-Leu-Ser-Gln-Asn-GluyAsn-His-Glu-Lys Glu-Phe-Thr-Val-Asn-Met-Arg-Cys-Pro-Tyr-Asn-Leu-Gly-Thr-Met-Lys-Val-Thr-Ile-Thr-Ala-Thr-Asn-Thr-Tyr-Asn-Asn-Ala-Ile-Leu-Val-Gln-Asn-Thr-Ser-Asn-Thr-Ser-Ser-Asp-Gly-Leu-Leu-Val-Tyr-Leu-Tyr-Asn-Ser-Asn-Ala-Gly-Asn-Ile-Gly-Thr-Ala-Ile-Thr-Leu-Gly-Thr-Pro-Phe Thr-Pro-Gly-Lys-Ile-Thr-Gly-Asn-Asn-Ala-Asp-Lys-Thr-Ile-Ser-Leu-His-Ala-Lys-Leu-Gly-Tyr-Lys-Gly-Asn-Met-Gln-Asn-Leu-Ile-Ala-Gly-Pro-Phe-Ser-Ala-Thr-Ala-Thr-Leu-Val-Ala-Ser-Tyr-Ser or any immunogenically active subsequence thereof.

9. An antigen according to claim 1 which has the following amino acid sequence:

Met-Ile-Arg-Leu-Ser-Leu-Phe-Ile-Ser-Leu-Leu-Leu-Thr-Ser-Val-Ala-Val-Leu-Ala-Asp-Val-Gln-Ile-Asn-Ile-Art-Gly-Asn-Val-Tyr-Ile-Pro-Pro-Cys-Thr-Ile-Asn-Asn-Gly-Gln-Asn-Ile-Val-Val-Asp-Phe-Gly-Asn-Ile-Asn-Pro-Glu-His-Val-Asp-Asn-Ser-Arg-Gly-Glu-Val-Thr-Lys-Thr Ile-Ser-Ile-Ser-Cys-Pro-Tyr-Lys-Ser-Gly-Ser-Leu-Trp-Ile-Lys-Val-Thr-Gly-Asn-Thr-Met-Gly-Gly-Gly-Gln-Asn-Asn-Val-Leu-Ala-Thr-Asn-Ile-Thr-His-Phe-Gly-Ile-Ala-Leu-Tyr-Gln-Gly-Lys-Gly-Met-Ser-Thr-Pro-Leu-Ile-Leu-Gly-Asn-Gly-Ser-Gly-Asn-Gly-Tyr-Gly-Val-T r-Ala-Gly-Leu-Asp-Thr-Ala-Arg-Ser-Thr-Phe-Thr-Phe-Thr-Ser-Val-Pro-Phe-Arg-Asn-Gly-Ser-Gly-Ile-Leu-Asn-Gly-Gly-Asp-Phe-Gln-Thr-Thr-Ala-Ser-Met-Ser-Met-Ile-Tyr-Asn or any immunogenically active subsequence thereof.

10. An antigen according to claim 1 which has the following amino acid sequence:

Met-Lys-Lys-Trp-Phe-Pro-Ala-Phe-Leu-Phe-Leu-Ser-Leu-Ser-Gly-Gly-Asn-Asp-Ala-Leu-Ala-Gly-Trp-His-Asn-Val-Met-Phe-Tyr-Ala-Phe-Asn-Asp-Tyr-Leu-Thr-Thr-Asn-Ala-Gly-Asn-Val-Lys-Val-Ile-Asp-Gln-Pro-Gln-Leu-Tyr-Ile-Pro-Trp-Asn-Thr-Gly-Ser-Ala-Thr-Ala-Thr-Tyr-Tyr Ser-Cys-Ser-Gly-Pro-Glu-Phe-Ala-Ser-Gly-Val-Tyr-Phe-Gln-Glu-Tyr-Leu-Ala-Trp-Met-Val-Val-Pro-Lys-His-Val-Tyr-Thr-Asn-Glu-Gly-Phe-Asn-Ile-Phe-Leu-Asp-Val-Gln-Ser-Lys-Tyr-Gly-Trp-Ser-Met-Glu-Asn-Glu-Asn-Asp-Lys-Asp-Phe-Tyr-Phe-Phe-Val-Asn-Gly-Tyr-Glu-Trp-Asp Thr-Trp-Thr-Asn-Asn-Gly-Ala-Arg-Ile-Cys-Phe-Tyr-Pro-Gly-Asn-Met-Lys-Gln-Leu-Asn-Asn-Lys-Phe-Asn-Asp-Leu-Val-Phe-Arg-Val-Leu-Leu-Pro-Val-Asp-Leu-Pro-Lys-Gly-His-Tyr-Asn-Phe-Pro-Val-Arg-Tyr-Ile-Arg-Gly-Ile-Gln-His-His-Tyr-Tyr-Asp-Leu-Trp-Gln-Asp-His-Tyr-Lys Lys-Met-Pro-Tyr-Asp-Gln-Ile-Lys-Gln-Leu-Pro-Ala-Thr-Asn-Thr-Leu-Met-Leu-Ser-Phe-Asp-Asn-Val-Gly-Gly-Cys-Gln-Pro-Ser-Thr-Gln-Val-Leu-Ash-Ile-Asn-His-Gly-Ser-Ile-Val-Ile-Asp-Arg-Ala-Asn-Gly-Asn-Ile-Ala-Ser-Gln-Thr-Leu-Ser-Ile-Tyr-Cys-Asp-Val-Pro-Val-Ser-Val Lys-Ile-Ser-Leu-Leu-Arg-Asn-Thr-Pro-Pro-Ile-Tyr-Asn-Asn-Asn-Lys-Phe-Ser-Val-Gly-Leu-Gly-Asn-Gly-Trp-Asp-Ser-Ile-Ile-Ser-Leu-Asp-Gly-Val-Glu-Gln-Ser-Glu-Glu-Ile-Leu-Arg-Trp-Tyr-Thr-Ala-Gly-Ser-Lys-Thr-Val-Lys-Ile-Glu-Ser-Arg-Leu-Tyr-Gly-Glu-Glu-Gly-Lys-Arg Lys-Pro-Gly-Glu-Leu-Ser-Gly-Ser-Met-Thr-Met-Val-Leu-Ser-Phe-Pro or any immunologically active subsequence thereof.

* * * * *